United States Patent [19]

Yoshinaga et al.

[11] Patent Number: 4,775,223
[45] Date of Patent: Oct. 4, 1988

[54] LACTIC ACID DERIVATIVE, LIQUID CRYSTAL COMPOSITION CONTAINING SAME AND LIQUID CRYSTAL DEVICE

[75] Inventors: Kazuo Yoshinaga, Machida; Kazuharu Katagiri, Tama, both of Japan

[73] Assignee: Canon Kabushiki Kaisha, Tokyo, Japan

[21] Appl. No.: 776,963

[22] Filed: Sep. 17, 1985

[30] Foreign Application Priority Data

| Sep. 20, 1984 | [JP] | Japan | 59-195770 |
| Nov. 7, 1984 | [JP] | Japan | 59-233269 |
| Jun. 19, 1985 | [JP] | Japan | 60-133527 |
| Jun. 19, 1985 | [JP] | Japan | 60-133528 |
| Jun. 20, 1985 | [JP] | Japan | 60-134835 |
| Jun. 20, 1985 | [JP] | Japan | 60-134836 |

[51] Int. Cl.$^4$ .............. G02F 1/13; C09K 19/22; C09K 19/52; C09K 19/34
[52] U.S. Cl. .............. 350/333; 252/299.01; 252/299.6; 252/299.61; 252/299.63; 252/299.64; 252/299.65; 252/299.66; 252/299.67; 252/299.68; 252/299.4; 534/566; 534/577; 534/573; 534/649; 534/852; 350/350 S; 350/340; 350/346; 350/351
[58] Field of Search ......... 252/299.01, 299.6, 299.61, 252/299.63, 299.64, 299.65, 299.66, 299.67, 299.68, 299.4; 350/350 S, 333, 340, 346, 351; 534/566, 577, 649, 855, 852, 573

[56] References Cited

U.S. PATENT DOCUMENTS

| 4,556,727 | 12/1985 | Walba | 252/299.67 |
| 4,576,732 | 3/1986 | Isogai et al. | 252/299.65 |
| 4,592,858 | 6/1986 | Higuchi et al. | 252/299.66 |
| 4,613,209 | 9/1986 | Goodby et al. | 350/350 S |
| 4,638,073 | 1/1987 | Walba et al. | 252/299.61 |

FOREIGN PATENT DOCUMENTS

| 0110299 | 6/1984 | European Pat. Off. | 252/299.65 |
| 3419223 | 12/1984 | Fed. Rep. of Germany . | |
| 57/176267 | 10/1982 | Japan | 560/72 |
| 2142625 | 1/1985 | United Kingdom . | |

OTHER PUBLICATIONS

Aguilera et al, CA 103:5971x (Jul. 1985).
Chem. Abs., vol. 87, No. 12, 86692h (1977).
Chem. Abs., vol. 82, No. 25, 169928n (1975).
Chem. Abs., vol. 75, No. 9, 62915j (1971).
Chem. Abs., vol. 103, No. 1, 5971x (1985).

Primary Examiner—Teddy S. Gron
Assistant Examiner—J. E. Thomas
Attorney, Agent, or Firm—Fitzpatrick, Cella, Harper & Scinto

[57] ABSTRACT

An optically active lactic acid derivative represented by the following formula (I):

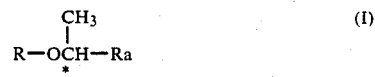

wherein R is a saturated or unsaturated hydrocarbon group of a linear, branched or cyclic structure having 4 to 20 carbon atoms; Ra is —CO—Rb or —CH$_2$—Rc wherein Rb is a releasable chemically active group, and Rc is a releasable chemically active group; and C with * represents an asymmetric carbon atom.

31 Claims, 11 Drawing Sheets

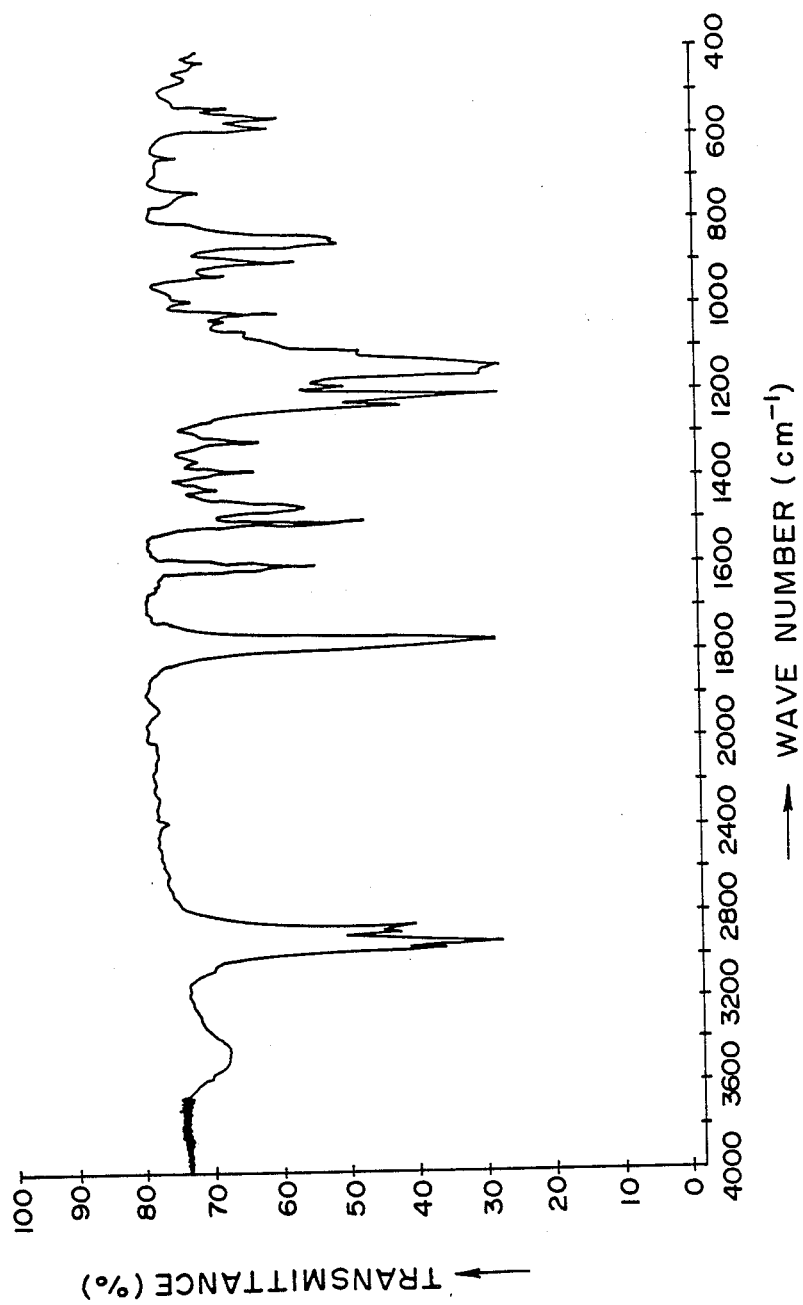
F I G. 2

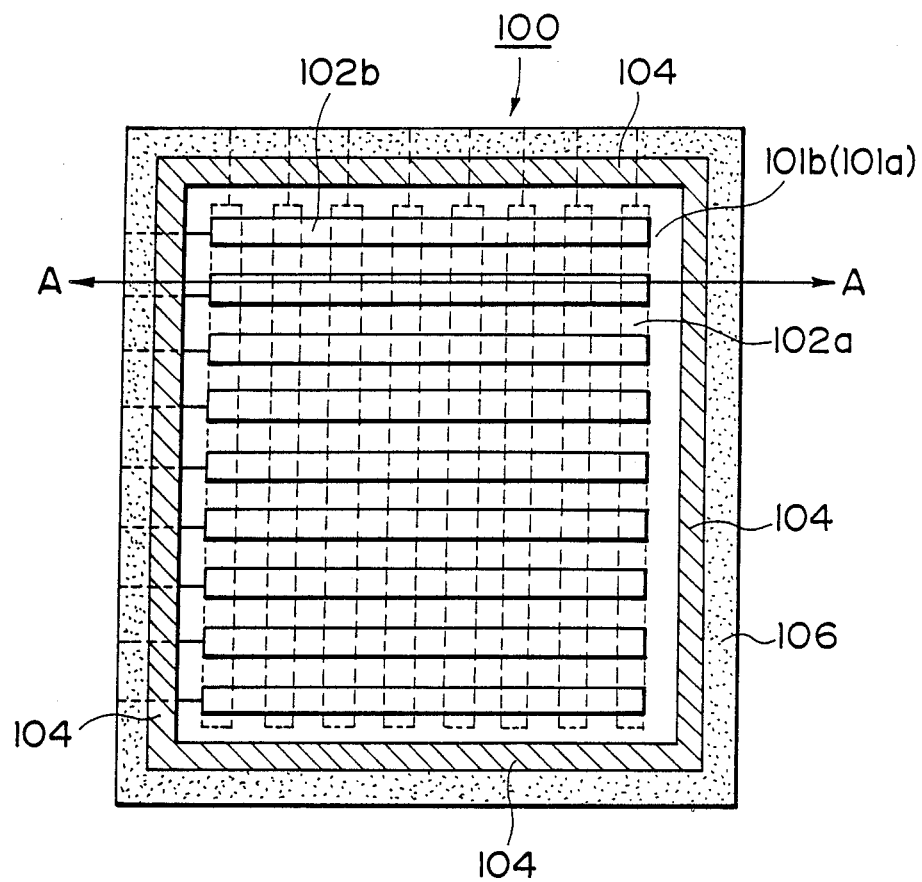
F I G. 6A

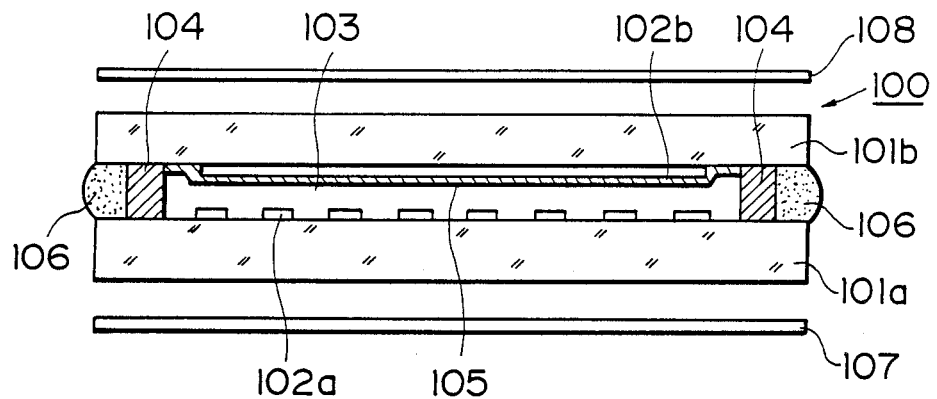
F I G. 6B
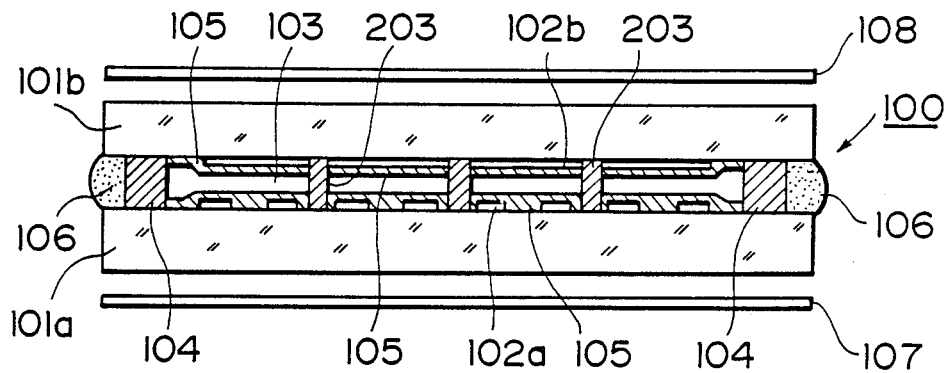
F I G. 7

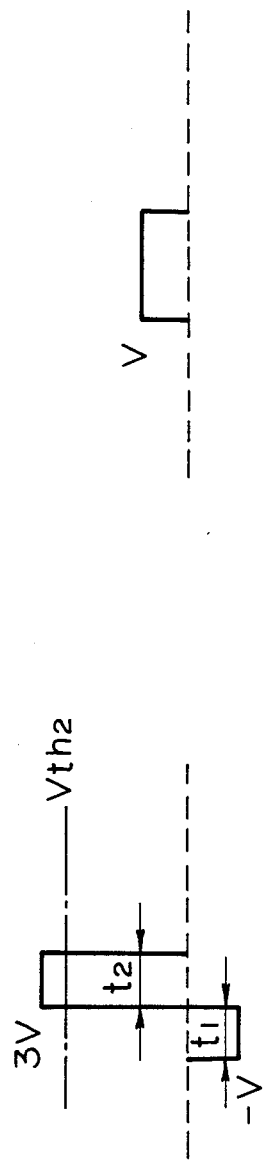
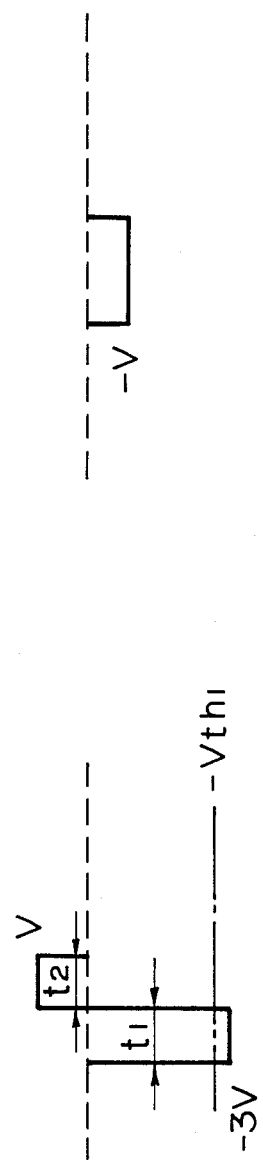
FIG. 11A  FIG. 11C
FIG. 11B  FIG. 11D

LACTIC ACID DERIVATIVE, LIQUID CRYSTAL COMPOSITION CONTAINING SAME AND LIQUID CRYSTAL DEVICE

FIELD OF THE INVENTION AND RELATED ART

The present invention relates to a lactic acid derivative capable of being readily modified with respect to its molecular structure and which has optical activity, and to a composition containing the lactic acid derivative. More specifically, the present invention relates to a lactic acid derivative, to a liquid crystal composition containing the same adapted for use in liquid crystal devices such as display devices and optical shutters, and also to a liquid crystal device using the same.

The lactic acid derivative of the present invention is particularly useful as an optically active intermediate for synthesis of functional materials necessary for production of various optical devices which are characterized by their optical activity. Examples of such optical devices characterized by optical activity or optical modulation include the following:

(1) Those utilizing a cholesteric-nematic phase transition in a liquid crystal state (J. J. Wysoki, A. Adams and W. Haas: Phys. Rev. Lett., 20, 10204 (1968));

(2) Those utilizing the guest-host effect of the White-Taylor type in a liquid crystal state (D. L. White and G. N. Taylor: J. Appl. Phys., 45, 4718 (1974));

(3) Those utilizing a ferroelectric liquid crystal effect of a chiral smectic C phase, H phase, F phase, I phase or G phase (N. A. Clark and S. T. Lagerwall: Appl. Phys, Lett., 36, 899 (1980));

(4) Others include notch filters or bond path filters utilizing selective scattering characteristics of a material having a cholesteric phase in the liquid crystal state when fixed in a matrix (F. J. Kahn: Appl. Phys. Lett., 18, 231 (1971)); and circular polarization beam splitters utilizing circular polarization characteristics (S. D. Jacobs, SPIE, 37, 98 (1981)).

These optical devices are important as display devices and modulation devices, while the explanation of the individual systems is left to the respective references and omitted.

Heretofore, as optically active intermediates for synthesizing functional materials necessary for such optical devices characterized by optical activity, compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

However, these intermediates involve respective problems as follows. Optically active chain hydrocarbon derivatives are difficult to modify structurally and very expensive except for a particular class thereof. Amino acid derivatives are relatively cheap and easy to modify, whereas N-hydrogens therein are chemically active and liable to cause hydrogen bonding or other chemical reactions so that the performance of the resultant functional material can be restricted thereby. Camphor derivatives and cholesterol derivatives are difficult to modify and steric hindrance is liable to provide ill effects to the performances of the resultant functional materials.

These problems have provided great difficulties in developing various functional materials.

On the other hand in the field of liquid crystal devices, there have been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters Vol. 18, No. 4 (Feb. 15, 1971) pp. 127–128. In this type of liquid crystal device, the number of picture elements have been restricted, because there is a problem that a crosstalk phenomenon occurs when a device of a matrix electrode structure with a high density of picture elements is driven according to a time-sharing or time-division driving scheme.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devides, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924).

As the bistable liquid crystal, a ferroelectric crystal showing a chiral smectic C phase (SmC*) or H phase (SmH*) is generally used.

Such a ferroelectric liquid crystal has bistability, i.e., has two stable states comprising a first stable state and a second stable state. Accordingly, in contrast to the conventional TN-type liquid crystal in the above-mentioned device, the liquid crystal is oriented to the first stable state in response to one electric field vector and to the second stable state in response to the other electric field vector. Further, this type of liquid crystal very quickly assumes either of the above-mentioned two stable states in response to an electric field applied thereto and retains such state in the absence of an electric field. By utilizing these properties, essential improvements can be attained with respect to the above-mentioned difficulties involved in the conventional TN-type liquid crystal device.

However, in order that an optical modulation device in which a liquid crystal having bistability is used can realize desired driving characteristics, it is required that a liquid crystal disposed between a pair of parallel base plates has a molecule arrangement such that molecules can effectively be switched between the two stable states independent of the application of an electric field. For instance, in connection with ferroelectric liquid crystals having SmC*- or SmH*-phase, it is required that there is a region (monodomain) where liquid crystal layers having SmC*- or SmH*-phase are vertical to the surfaces of base plates, i.e., the liquid crystal axis is aligned substantially parallel with the surfaces. However, with optical modulation devices in which a liquid crystal having bistability is used, the orientation of the liquid crystal having such a monodomain structure has not satisfactorily been formed, thus failing to obtain sufficient display characteristics.

For instance, in order to give such an orientation, Clark et al. have proposed a method of applying an electric field, a method of applying shearing stress, and a method of arranging ridges parallel to each other at small intervals between the base plates, etc. However, these methods could not necessarily provide satisfactory results. For instance, the method of applying an electric field has drawbacks in that it requires a large scale apparatus and is not compatible with a thin layer cell having excellent operational characteristics. Further, the method of applying a shearing stress has drawback that it is not compatible with a method of filling a liquid crystal after a cell is prepared. Furthermore, the method of arranging parallel ridges within the cell cannot provide stable orientation effect by itself.

Further, when the liquid crystal device showing bistability is driven for line-by-line writing operation, some of picture elements which have been written corresponding to information signals for the picture can change the stable orientation of the liquid crystal from the orientation state for displaying the written signal to the other orientation state to erase several of the written picture elements. This is for example, the phenomenon wherein picture elements which have been written to dsplay "white" signal are reversed to the state for displaying "black" signal. Such reversal phenomena makes it difficult to use the ferroelectric liquid crystal device as a display device.

SUMMARY OF THE INVENTION

A principal object of the present invention is to provide a significant step to the solution of the above described problems. More specifically, an object of the invention is to provide a compound which can be combined with an intermediate for a functional material having appropriate inter-molecular force and shape without imparing an optical activity, and therefore be susceptible of arbitrary molecular modification.

A specific object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146(1964), and to provide a liquid crystal composition containing at least one of such mesomorphic compounds. A further object of the present invention is to provide a compound capable of easily controlling the hydrophobic group and being stably formed into a film when applied to the LB (Langmuir-Blodget) film process for preparing an accumulation of single molecular films.

Another object of the present invention is, in view of th above-mentioned circumstances, to provide a ferroelectric liquid crystal device which has potential adaptability to a display device having a high response speed characteristic, a high density of picture elements and a large display area or an optical shutter having a high shutter speed and to have the ferroelectric liquid crystal device fully perform by improving the monodomain formation characteristic or the initial alignment characteristic which has been the principal problem of the device.

Another object of the present invention is to provide a liquid crystal device for time-sharing driving wherein the above mentioned reversal phenomenon has been prevented and a display state corresponding to an information signal can be stably retained for a period of one frame or one field.

According to one aspect of the present invention, there is provided an optically active lactic acid derivative represented by the following formula (I):

wherein R is a saturated or unsaturated hydrocarbon group of a linear, branched or cyclic structure having 4 to 20 carbon atoms; Ra is —CO—Rb or —CH$_2$—Rc wherein Rb is a releasable chemically active group, and Rc is a releasable chemically active group; and C with * represents an asymmetric carbon atom.

According to another aspect of the present invention, there is provided a lactic acid derivative

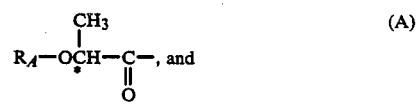

wherein $R_A$ and $R_B$ are respectively a saturated or unsaturated hydrocarbon group of a linear, branched or cyclic structure having 1 to 20 carbon atoms and C with * represents an asymmetric carbon atom.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 6A is a plan view showing an example of the liquid crystal device according to the present invention, FIG. 6B is a sectional view taken along the line A—A in FIG. 6A;

FIG. 7 is a sectional view showing another example of the liquid crystal device according to the present invention;

FIGS. 11A to 11D illustrate waveforms applied to respective picture elements.

DETAILED DESCRIPTION OF THE INVENTION

Figure 1:
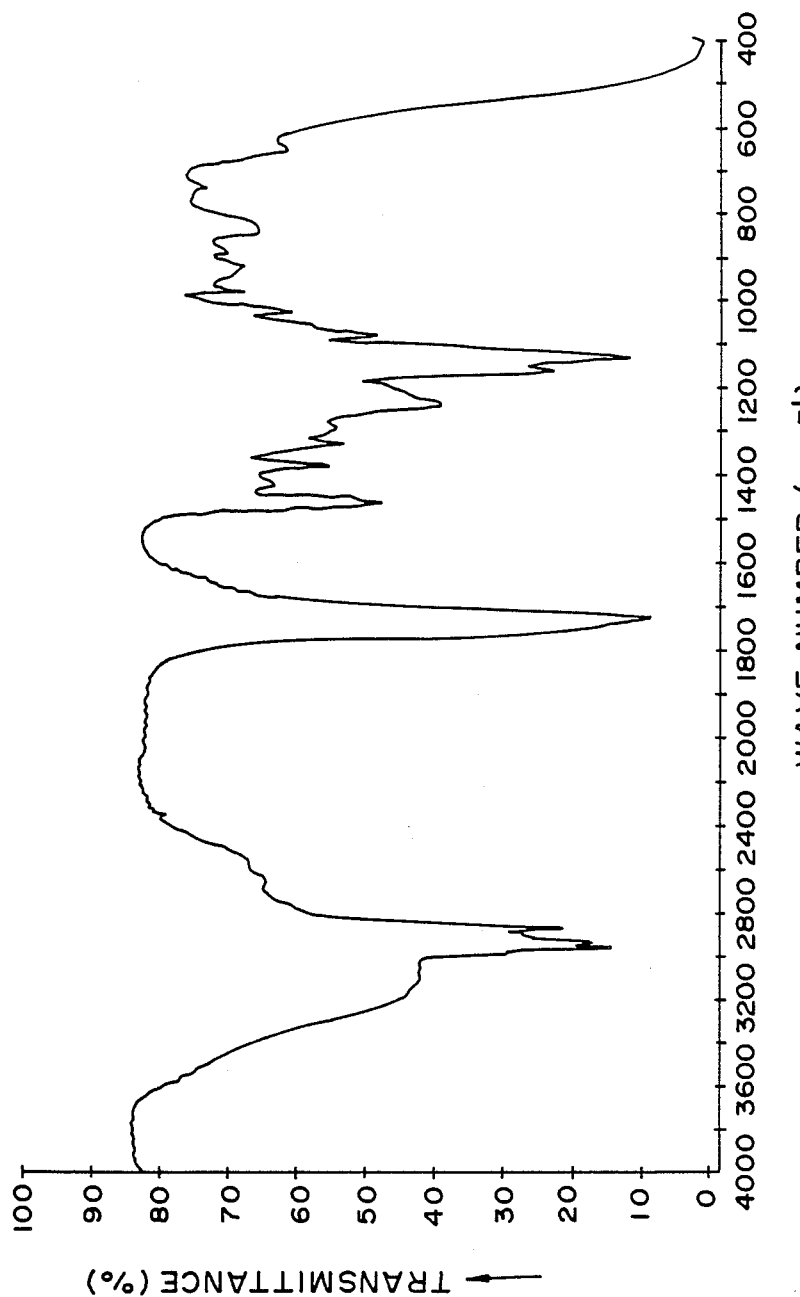
FIG. 1 shows an IR spectrum (KBr disk method) of a compound obtained in Example 4, FIG. 2 an IR spectrum (KBr disk method) of a compound obtained in Example 9, and FIG. 3 an IR spectrum (Bulk method)

As stated hereinbefore, the present invention provides an optically active lactic acid derivative of the following formula (I):

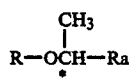
(I)

wherein R is a saturated or unsaturated hydrocarbon group of a linear, branched or cyclic structure having 4 to 20 carbon atoms; Ra is —CO—Rb or —CH$_2$—Rc wherein Rb is a releasable chemically active group such as —OH (hydroxy) group, halogen atom, alkoxy group or phenoxy group, and Rc is a releasable chemically active group such as hydroxy group, halogen atom, phenoxy group, toluenesulfonic acid group,

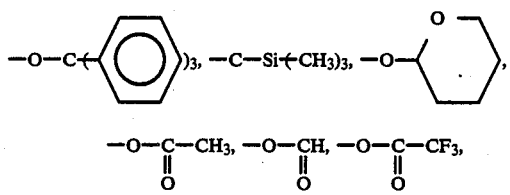

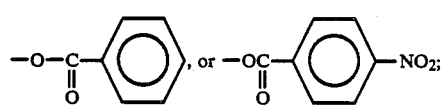

and C with * represents an asymmetric carbon atom; and a lactic acid derivative having an optically active group represented by the following formula (A) or (B):

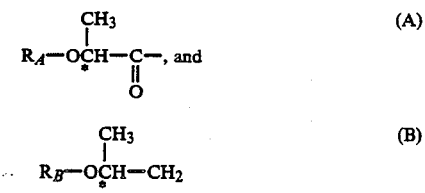

wherein $R_A$ and $R_B$ are respectively a saturated or unsaturated hydrocarbon group of a linear, branched or cyclic structure having 1 to 20 carbon atoms and C with * represents an asymmetric carbon atom.

More specifically the following compounds of the formulae (1) to (8) are provided:

Formula (1)
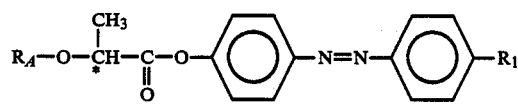

(2)
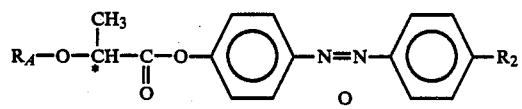

(3)
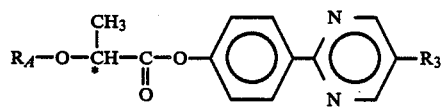

(4)
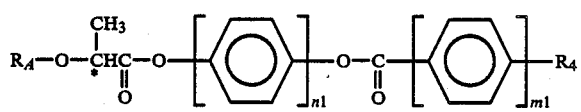

(5)
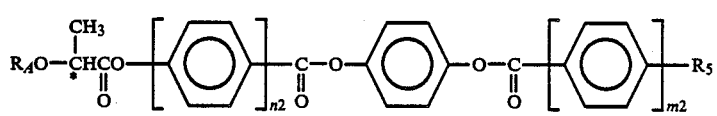

(6)
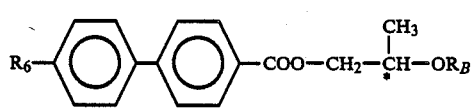

(7)
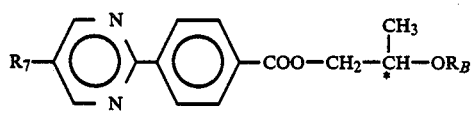

Formula (8)

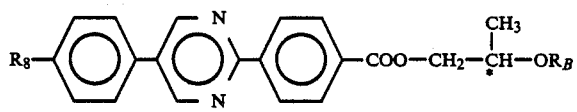

In the above formulae, $R_A$ and $R_B$ are respectively a linear, branched or acyclic saturated or unsaturated hydrocarbon group having 1 to 20 carbon atoms. If they have 21 or more carbon atoms, the resultant functional material containing the compound is caused to have an undersirably increased viscosity or molar volume. On the other hand, if the group $R_A$ or $R_B$ contains 3 or less carbon atoms, they can lose a desired characteristic as a terminal group. In view of a suitable viscosity and molar volume, it is further preferred that the groups $R_A$ and $R_B$ have 4 to 16 carbon atoms.

Specific examples of the groups R, $R_A$ and $R_B$ include linear alkyls, branched alkyls, cycloalkyls, linear alkenyls, branched alkenyls, cycloalkenyls, linear alkadienyls, branched alkadienyls, cycloalkadienyls, linear alkatrienyls, branched alkatrienyls, linear alkynyls, branched alkynyls, branched alkynyls, and aralkyls.

The groups $R_1$-$R_8$ are respectively an alkyl or alkoxy group having 1 to 20 carbon atoms, while $n_1$, $n_2$, $m_1$ and $m_2$ are respectively 1 or 2.

The groups Rb and Rc can be easily replaced by another groups by reaction with a reagent under appropriate conditions. In this instance, mesomorphic compounds and other functional materials may be obtained by using various reagents.

In order to synthesize functional materials adapted for use in optical devices, modulation devices, etc., it is effective to combine the optically active lactic acid derivative without impairing the optical activity with an intermediate of functional material having an appropriate intermolecular force and shape and susceptible of molecular control. Examples of such intermediates of functional material effective for combination with the lactic acid derivative according to the present invention include azo derivatives, azoxy derivatives, ring-assembly hydrocarbon derivatives, condensed polycyclic hydrocarbon derivatives, heterocyclic derivatives, condensed heterocyclic derivatives, and ring-assembly heterocyclic derivatives. More specifically, there are included azobenzene derivatives, azoxybenzene derivatives, biphenyl derivatives, terphenyl derivatives, phenylcyclohexane derivatives, benzoic acid derivatives, pyrimidine derivatives, pyrazine derivatives, pyridine derivatives, stilbene derivatives, tolan derivatives, chalcone derivatives, bicyclohexane derivatives, and cinnamic acid derivatives.

In the following is explained a process of synthesizing a compound having a releasable chemically active group Rb as an example of the lactic acid derivative shown by the formula (I) according to the present invention:

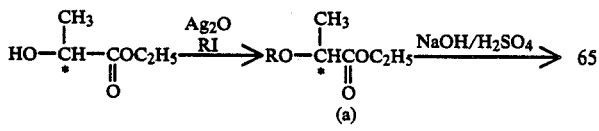

(a)

-continued

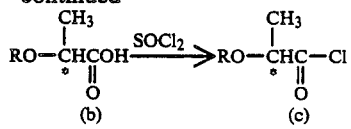

(b)           (c)

Thus, a compound wherein the Rb is an alkoxyl (the compound of the above formula (a)) may be produced by reacting a lactic acid ester and a hydrocarbon iodide in the presence of $Ag_2O$. In this instance, it is preferred that the lactic acid ester and the hydrocarbon iodide are charged in a vessel and mixed, and then $Ag_2O$ is charged into the mixture.

Further, a compound wherein the Rb is a hydroxyl (the compound of the above formula (b)) may be synthesized by hydrolyzing the compound of the formula (a) with a base and then neutralizing the hydrolyzed product.

Then, a compound wherein the Rb is a halogen atom (the compound of the formula. (c)) may be produced by reacting the compound of the above formula (b) with a halogenation agent such as $SOCl_2$ and $PCl_5$.

The RI in the above reaction scheme may be selected from a wide scope of iodides. Examples thereof include linear saturated hydrocarbon iodides such as iodobutane, iodopentane, iodohexane, iodoheptane, iodooctane, iodononane, iododecane, iodoundecane, iodododecane, iodotridecane, iodotetradecane, iodopentadecane, iodohexadecane, iodoheptadecane, iodooctadecane, iodononadecane, and iodocicosane; branched saturated hydrocarbon iodides such as 2-iodobutane, 2-iodo-2-methylpropane and 1-iodo-3-methylbutane; cyclic unsaturated hydrocarbon iodides such as iodobenzyl iodophenacyl and 3-iodo-1-cyclohexene; and cyclic saturated hydrocarbon iodides such as iodocyclopentane, iodocyclohexane, 1-iodo-3-methylcyclohexane, iodocycloheptane and iodocyclooctane.

An appropriate RI may be selected from the iodides as described above to obtain an optically active lactic acid derivative according to the present invention. Optical rotation data of some examples of the optically active lactic acid derivatives obtained from the linear saturated hydrocarbon iodides are shown in the following Table 1.

TABLE 1

$$R-O-\overset{CH_3}{\underset{*}{C}H}\overset{}{\underset{\parallel}{C}}OC_2H_5$$
$$\phantom{R-O-CH}O$$

| R | $[\alpha]_D$ | R | $[\alpha]_D$ |
|---|---|---|---|
| $C_4H_9$— | −73° | $C_{12}H_{25}$— | −42° |
| $C_5H_{11}$— | −64° | $C_{13}H_{27}$— | −40° |
| $C_6H_{13}$— | −58° | $C_{14}H_{29}$— | −39° |
| $C_7H_{15}$— | −51° | $C_{15}H_{31}$— | −36° |
| $C_8H_{17}$— | −50° | $C_{16}H_{33}$— | −35° |
| $C_9H_{19}$ | −49° | $C_{17}H_{35}$— | −33° |
| $C_{10}H_{21}$— | −48° | $C_{18}H_{37}$— | −30° |
| $C_{11}H_{23}$— | −44° | $C_{19}H_{39}$— | −31° |

TABLE 1-continued $$R-O-\overset{*}{\underset{\underset{O}{\|}}{C}}H\underset{CH_3}{|}COC_2H_5$$

| R | $[\alpha]_D$ | R | $[\alpha]_D$ |
|---|---|---|---|
| $C_{20}H_{41}-$ | $-28°$ | | |

By using various lactic acid derivatives obtained in the manner as described above, mesomorphic compounds represented by the formulae (II) and (III) were obtained along the following reaction scheme.

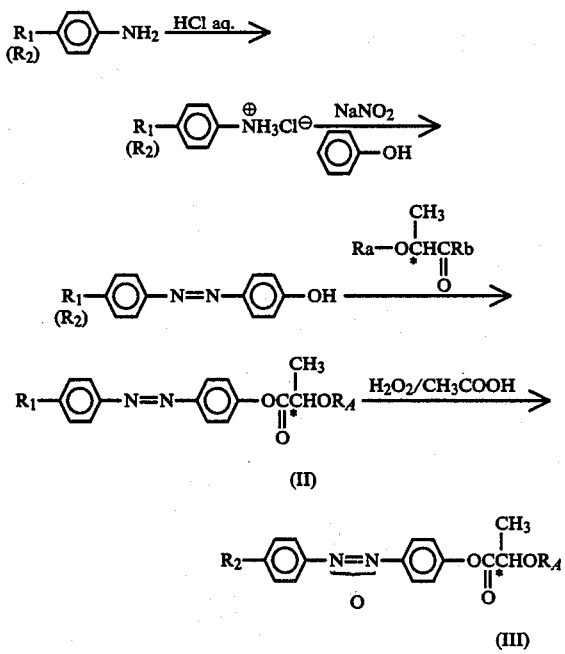

(In the above formulae (II) and (III), $R_A$ is a linear, branched or cyclic saturated or unsaturated hydrocarbon groups having 1 to 20 carbon atoms, and $R_1$ and $R_2$ are respectively an alkyl or alkoxy group having 1 to 20 carbon atoms.)

Some representative examples of the mesomorphic compounds are as follows.

(1) 4'-hexyl-4-α-butoxypropanoyloxyazobenzene
(2) 4'-heptyl-4-α-butoxypropanoyloxyazobenzene,
(3) 4'-octyl-4-α-butoxypropanoyloxyazobenzene,
(4) 4'-hexyloxy-4-α-butoxypropanoyloxyazobenzene,
(5) 4'-octyl-4-α-heptyloxypropanoyloxyazobenzene,
(6) 4'-hexyloxy-4-α-heptyloxypropanoyloxyazobenzene,
(7) 4'-hexyloxy-4-α-butoxypropanoyloxyazobenzene,
(8) 4'-octyl-4-α-heptyloxypropanoyloxyazoxybenzene,
(9) 4'-hexyloxy-4-α-heptyloxypropanoyloxyazoxybenzene,
(10) 5-decyl-2-(4'-α-pentyloxypropanoyloxyphenyl)-pyrimidine,
(11) 4'-α-octadecyloxypropanoyloxyphenyl 4-octyloxybenzoate,
(12) 4'-α-dodecyloxypropanoyloxyphenyl 4-octyloxybenzoate,
(13) 4''-α-heptyloxypropanoyloxyphenyl 4-heptylbiphenylcarboxylate,
(14) 4'-(4''-α-octyloxypropanoyloxybenzoyloxy)phenyl 4-octyloxybiphenylcarboxylate,
(15) 4'-(4''-α-nonyloxypropanoyloxybenzoyloxy)phenyl 4-pentyloxybenzoate,
(16) 4'-(4''-α-dodecyloxypropanoyloxybenzoyloxy)phenyl 4-heptylbiphenylcarboxylate,
(17) 4'-(4''-α-pentyloxypropanoyloxybiphenylcarboxyl)phenyl 4-heptylbiphenylcarboxylate,
(18) 5-nonyl-2-(α-propyloxypropanoyloxyphenyl)-pyrimidine,
(19) 4'-(4''-α-ethoxypropanoyloxybenzoyloxy)phenyl 4-pentylbiphenylcarboxylate.

Then, an exemplary process for sythesizing a compound having a releasable chemically active group Rc as an example of the lactic acid derivative according to the present invention is explained hereinbelow.

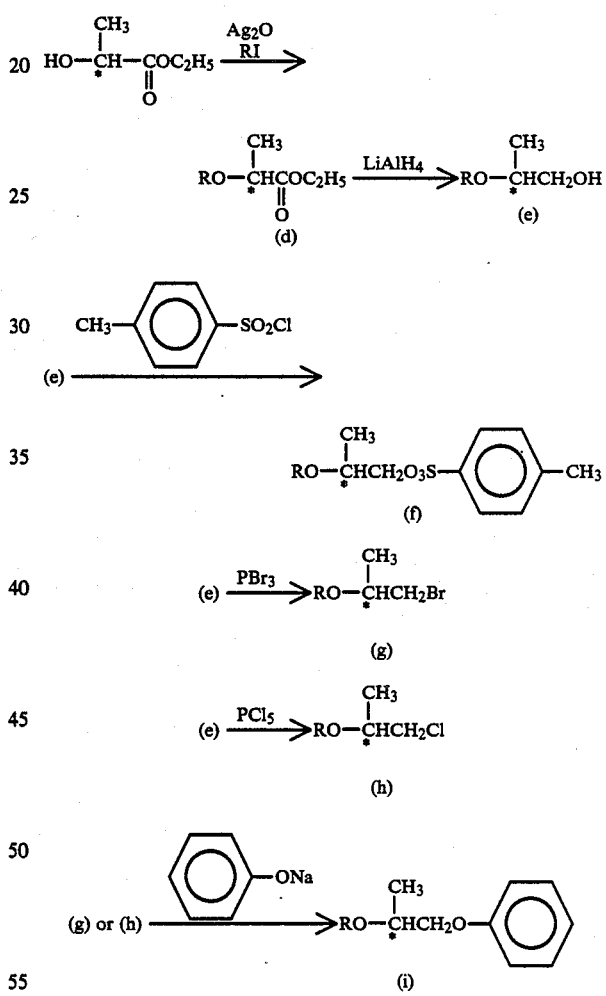

A compound of the above formula (d) may be obtained by reacting a lactic acid ester and a hydrocarbon iodide in the presence of Ag₂O. In this instance, it is preferred that the lactic acid ester and the hydrocarbon iodide are charged in a vessel and mixed, and then Ag₂O is charged into the mixture.

Further, a compound wherein the Rc is a hydroxyl (the compound of the above formula (e)) may be synthesized by treating the compound of the formula (d) with a reducing agent such as LiAlH₄.

Then, a compound wherein the Rc is a halogen atom may be produced by reacting the compound of the above formula (e) with a halogenation agent such as PBr$_3$, SOCl$_2$ and PCl$_5$.

The RI in the above reaction scheme may be the same as those described above with reference to the compounds of the formulas (b) and (c). Optical rotation data of examples of the optically active lactic acid derivatives obtained from the linear saturated hydrocarbon iodides are shown in the following Table 2.

TABLE 2

$$R-O\overset{*}{C}HCH_2OH$$
(with CH$_3$ on the starred carbon)

| R | $[\alpha]_D$ | R | $[\alpha]_D$ |
|---|---|---|---|
| C$_4$H$_9$— | +24.4° | C$_{12}$H$_{25}$— | +13.0° |
| C$_5$H$_{11}$— | +22.1° | C$_{13}$H$_{27}$— | +13.2° |
| C$_6$H$_{13}$— | +20.1° | C$_{14}$H$_{29}$— | +12.9° |
| C$_7$H$_{15}$— | +17.4° | C$_{15}$H$_{31}$— | +12.6° |
| C$_8$H$_{17}$— | +17.2° | C$_{16}$H$_{33}$— | +12.2° |
| C$_9$H$_{19}$— | +16.1° | C$_{17}$H$_{35}$— | +12.0° |
| C$_{10}$H$_{21}$— | +16.1° | C$_{18}$H$_{37}$— | +12.2° |
| C$_{11}$H$_{23}$— | +14.3° | C$_{19}$H$_{39}$— | +11.5° |
|  |  | C$_{20}$H$_{41}$— | +11.2° |

By using various lactic acid derivatives obtained in the manner as described above, mesomorphic compounds represented by the formulas (IV)–(VI) were obtained along the following reaction schemes.

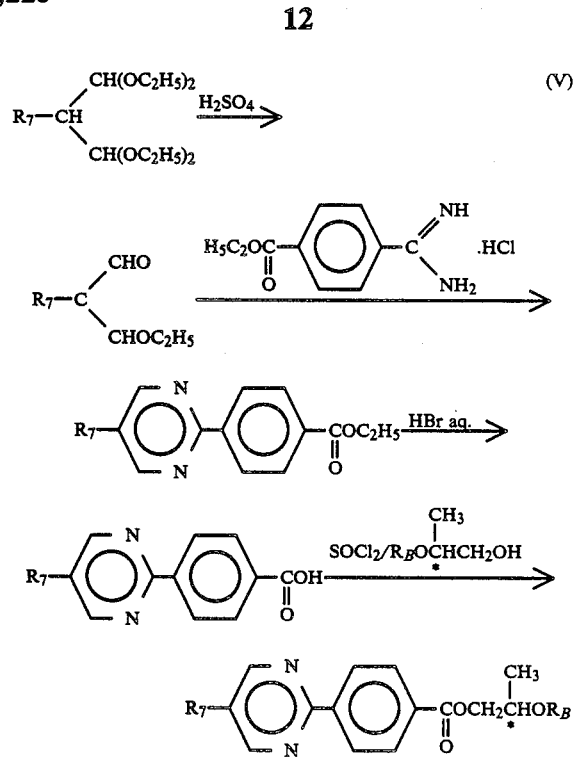

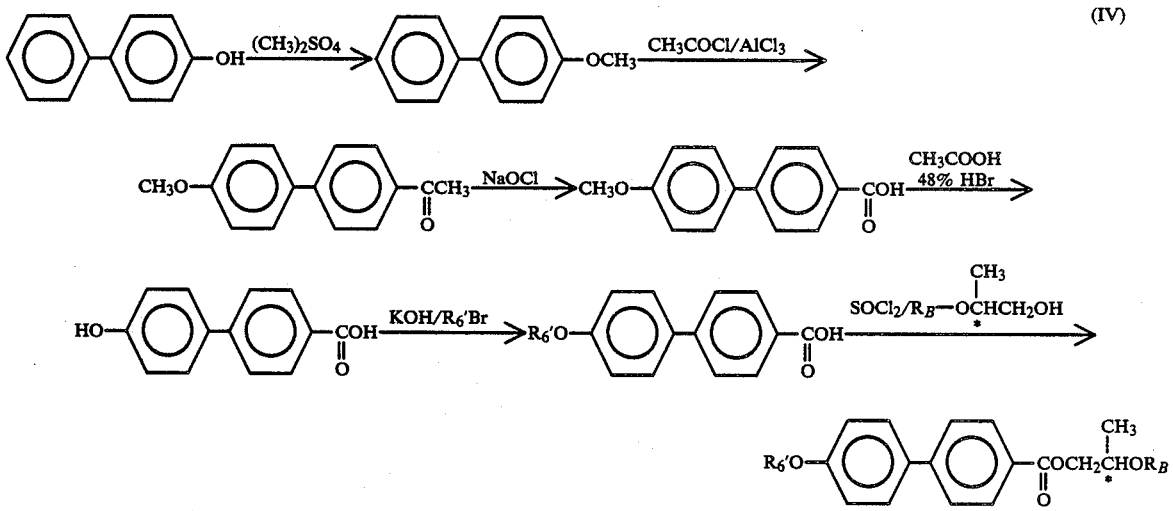

(In the above formula (IV), R$_B$ is a linear, branched or cyclic saturated or unsaturated hydrocarbon groups having 1 to 20 carbon atoms, and R$_6'$ is an alkyl or having 1 to 20 carbon atoms. The group R$_6'$ corresponds to R$_6$ in the formula (6) mentioned before in a case where it is an alkoxy group.

(In the above formula (V), R$_B$ is a linear, branched or cyclic saturated or unsaturated hydrocarbon groups having 1 to 20 carbon atoms, and R$_7$ is an alkyl or alkoxy group having 1 to 20 carbon atoms.)

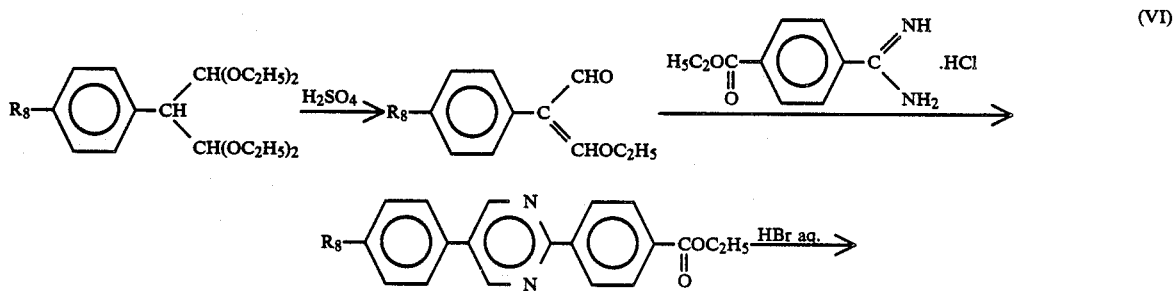

-continued

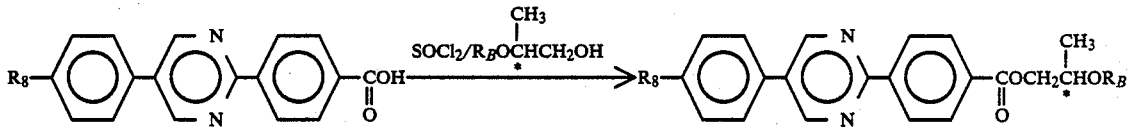

(In the above formula (VI), $R_B$ is a linear, branched or cyclic saturated or unsaturated hydrocarbon groups having 1 to 20 carbon atoms, and $R_8$ is an alkyl or alkoxy group having 1 to 20 carbon atoms.)

Some representative examples of the lactic acid derivatives are as follows.

(20) heptyloxypropyl-4'-octyloxybiphenyl-carboxylate,
(21) butoxypropyl-4'-octyloxybiphenyl-4-carboxylate,
(22) 2'-dodecyloxypropyl-4-(5-(4'-butylphenyl)-pyridine-2-yl)benzoate,
(23) 2'-decyloxypropyl-4-(5-heptylpyridine-2-yl)benzoate,
(24) α-propyloxypropyl-4'-heptyl-terphenylcarboxylate,
(25) 2'-ethoxypropyl-(5-4'-pentylcyclohexyl)pyrimidine-2-yl)benzoate,
(26) α-octadecyloxypropyl-4'-heptylbiphenyl-4-carboxylate.

A particularly preferred class of these lactic acid derivatives may be represented by the following formula (Q):

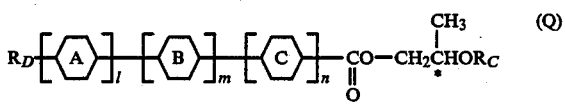

wherein $R_C$ is an alkyl group having 1–20 carbon atoms; $R_D$ is an alkyl or alkoxy group having 4 to 20 carbon atoms; l, m and n are respectively 0 or an integer satisfying the relationship: $3 \geq l+m+n \geq 1$; and

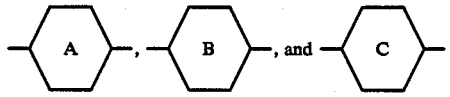

are 1,4-substituted 6-member ring groups such as hydrocarbon rings, heterocyclic groups and combination of these. The 1,4-substituted hydrocarbon ring may typically be a 1,4-substituted aromatic group such as 1,4-phenyl group, and an example of the heterocyclic group is 1,4-pyrimidinylene group.

When the lactic acid derivative according to the present invention is used, it is possible to obtain an optically active mesomorphic compound having a mesomorphicity-imparting skeletons such as those of azobenzene, azoxybenzene, biphenyl, phenylcyclohexane, benzoid acid, pyrimidine, pyrazine, pyridine, stilbene, tolan, chalcone, bicyclohexane, and cinnamic acid with side chains of arbitrarily controlled lengths, molecular weights and shapes, and thus an objective compound with desired physical properties. Heretofore, it has been possible only to change a side chain remote from an asymmetric carbon, whereas it has become possible to change both terminal groups according to the present invention. This is a very significant step to utilization of liquid crystals and LB films as functional elements and to molecular designing for desired purposes.

Further, the optically active lactic acid derivative according to the present invention is effectively used for providing a smectic liquid crystal with increased spontaneous polarization of ferroelectricity.

According to the present invention, the above mentioned mesomorphic compound is used alone or in combination of two or more species thereof to provide a liquid crystal composition. It is also possible to mix at least one of the mesomorphic compound with another mesomorphic compound, particularly a ferroelectric liquid crystal compound to provide a liquid crystal composition showing ferroelectricity. This is a particularly preferred embodiment of the present invention from the viewpoint of providing a ferroelectric liquid crystal with improved properties such as an increased spontaneous polarization. Specific examples of ferroelectric liquid crystal compounds as other liquid crystal components for producing such a liquid crystal composition are enumerated below:

A. Schiff base-type ferroelectric liquid crystal compound:

(1) DOBAMBC (p-decyloxybenzylidene-p'-amino-2-methylbutyl cinnamate)
(The compounds obtained by replacing the p-decyloxy group with an alkoxy group ranging from p-hexyloxy to p-decyloxy group in this series show ferroelectricity and may be used in the composition of the present invention.)

(2) DOBAMBCC (p-decyloxybenzylidene-p-amino-2-methylbutyl α-cyanocinnamate)
(The compound obtained by replacing the p-Decyloxy group with p-tetradecyloxy group also shows ferroelectricity.)

(3) OOBAMBCC (p-octyloxybenzylidene-p'-amino-2-methylbutyl α-chlorocinnamate)

(4) HOBACPC (p-hexyloxybenzylidene-p'-amino-2-chloropropyl cinnamate)
(The compounds having an alkoxy group ranging from p-hexyloxy to p-dodecyloxy in this series show ferroelectricity.)

(5) OOBAMBMC (p-octyloxybenzylidene-p'-amino-2-methylbutyl α-methylcinnamate)

(6) DOBMBA (p-decyloxybenzylidene-p'-(2-methyloxycarbonyl)aniline)
(The compounds having an alkoxy group ranging from p-heptyloxy to p-tetradecyloxy in this series show ferroelectricity.)

MBRA n=8 (S-4-O-(2-methyl)butylresorcilidene-4'-alkylaniline

Structure:

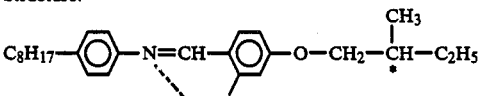

Molecular formula: $C_{26}H_{33}O_2N$
Molecular weight: 391.55
Transition temperature (°C.):

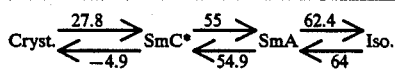

Herein, the abbreviations and symbols represent the following:
Cryst: crystal, SmC*: chiral smectic C phase, SmA: smectic A phase, Iso: isotropic phase.
(8) MORA 8 (S-4-O-(6-methyl)octylresorcylidene-4'-octylaniline)

Structure:

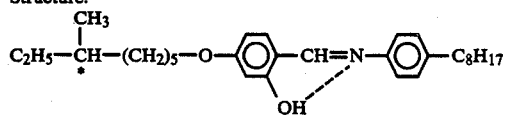

Molecular formula: $C_{30}H_{45}O_2N$
Transition temperatures (°C.):

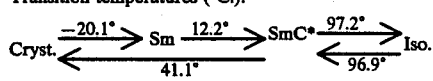

B. Ester-type ferroelectric liquid crystal compounds:
(1) 4-n-hexyloxyphenyl 4-(2''-methylbutyl)biphenyl-4'-carboxylate
(2) 4-(2'-methylbutyl)phenyl 4'-octylbiphenyl-4-carboxylate
(3) 2-(2'-methylbutyloxy)phenyl 4'-dodecyloxyphenyl-4-carboxylate
(The compound obtained by replacing the 2'-methylbutyloxy group with 4'-nonyloxy group also shows ferroelectricity.)

C. Azoxy-type ferroelectric liquid crystal compound:
(1) PACMB (p-azoxycinnamate 2-methylbutanol)

In a liquid crystal composition comprising a ferroelectric liquid crystal compound and a lactic acid derivative as described above, especially a lactic acid derivative of the above formulas (1)–(8), the lactic acid derivative may preferably be incorporated in an amount of 0.01 to 100 wt. parts for 100 wt. parts of the ferroelectric liquid crystal compound. If the amount is less than 0.01 wt. part, effects or performances of a ferroelectric liquid crystal such as those of varying the temperature range for exhibiting ferroelectric mesomorphism and extending the operation life cannot be attained. On the other hand, if the amount exceeds 100 wt. parts, the ferroelectric liquid crystal compound is so diluted as to show a lower performance. In a further preferred embodiment, the lactic acid derivative may be used in a proportion of 0.05 to 95 wt. parts for 100 wt. parts of the other liquid crystal component.

When the above-mentioned lactic acid derivative functions as a ferroelectric liquid crystal by itself, it may be mixed with a cholesteric liquid crystal compound as follows:

(A) Cholesteryl propionate

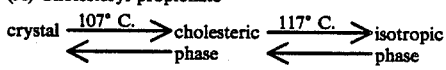

(B) Cholesteryl nonamate

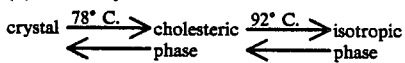

(C) Cholesteryl palmitate

(D) Cholesteryl benzoate

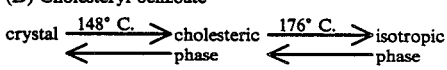

(E)

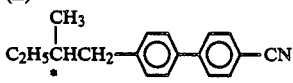

4-(2''-methylbutyl)-4'-cyanobiphenyl

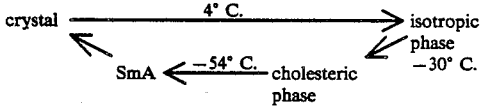

(F)

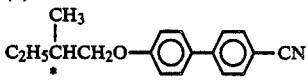

4-(2''-methylbutyloxy)-4'-cyanobiphenyl

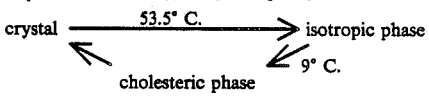

(G)

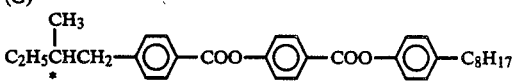

4-octylphenyl-4'-(4-β-methylbenzoyloxy)benzoate

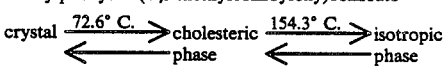

(H)

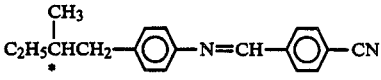

4-cyanobenzylidene-4'-(2-methylbutyl)aniline

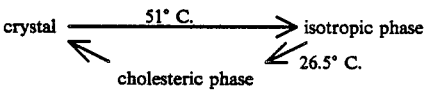

(I)

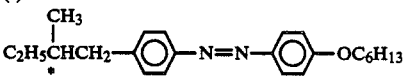

4-(2-methylbutyl)-4'-hexyloxyazobenzene

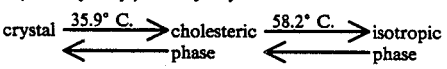

(J)

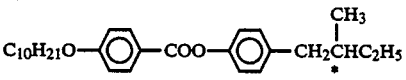

4-(2-methylbutyl)phenyl-4'-decyloxybenzoate

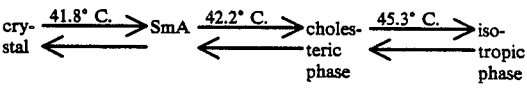

(K)

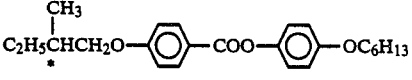

4-hexyloxy-4'-(2-methylbutyl)benzoate

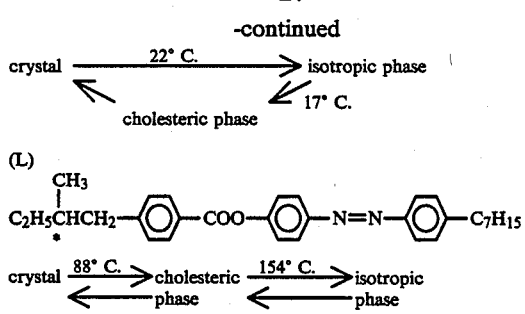

(L)

crystal $\xrightarrow{88°\text{ C.}}$ cholesteric $\xrightarrow{154°\text{ C.}}$ isotropic
         $\xleftarrow{\phantom{88°\text{ C.}}}$ phase      $\xleftarrow{\phantom{154°\text{ C.}}}$ phase

EXAMPLES

Hereinbelow, processes of preparing the compounds according to the present invention will be explained by way of specific examples.

In the following examples, the phrase transition temperature was measured by a DSC (differential scanning calorimeter) (SSC 580 DS, manufactured by Seiko Denshi K.K.), and the phase transition was confirmed by placing a liquid crystal sealed between glass plates in a copper block under temperature control and observing it through a ppolarizing microscope.

EXAMPLE 1

((−)-ethyl-2-butoxypropionate)

31.5 g of L-(+)-ethyl lactate and 107.3 g of 1-iodobutane were charged into a 4-necked flask, and freshly prepared $Ag_2O$ was added in 2 hours. The mixture was left standing at room temperature for 15 hours, then diluted with 200 ml of ether, filtered and subjected to distillation for removing the ether. The residue was washed with 100 ml of 5% aqueous KOH solution, dried with anhydrous $Na_2SO_4$ and subjected to reduced-pressure distillation to collect a fraction at 110° C./54 mmHg, whereby 23 g of (−)-ethyl-2-butoxypropionate was obtained. The optical rotation and IR (infrared absorption) peaks of the product were as follows:
$[\alpha]_D^{24°} = -73°$, IR: 1750, 1140 cm$^{-1}$.

EXAMPLE 2

((−)-ethyl-2-heptyloxypropionate)

64.7 g of L-(+)-ethyl lactate and 95.2 g of 1-iodoheptane were mixed, and freshly prepared $Ag_2O$ was added in 2 hours. The mixture was left standing at room temperature for 72 hours, then diluted with 400 ml of ether, filtrated and subjected to distillation for removing the ether. The residue was washed with 200 ml of 5% aqueous KOH solution, dried with anhydrous $Na_2SO_4$ and subjected to reduced-pressure distillation to collect a fraction at 122° C./12 mmHg, whereby 30 g of (−)-ethyl-2-heptyloxypropionate was obtained. The optical rotation and IR peaks of the product were as follows:
$[\alpha]_D^{24°} = -51°$, IR: 1750, 1130 cm$^{-1}$.

EXAMPLE 3

((−)-ethyl-2-dodecyloxypropionate)

47.0 g of L-(+)-ethyl lactate and 88.4 g of 1-iododecane were charged into a flask and mixed under an $N_2$ stream, and 42.1 g of freshly prepared $Ag_2O$ was added in 3 hours. The mixture was left standing at room temperature for 50 hours and then heated at 60°–70° C. for 4 hours on a water bath. The mixture was then diluted with 200 ml of ether, filtered and subjected to distillation for removing the ether. The residue was washed with 100 ml of 5% aqueous KOH solution, dried with anhydrous $Na_2SO_4$ and subjected to reduced-pressure distillation to collect a. fraction at 169° C./9 mmHg, whereby 22 g of (−)-ethyl-2-dodecyloxypropionate was obtained. The optical rotation and IR peaks of the product were as follows.
$[\alpha]_D^{23°} = -42°$, IR: 2920, 1750, 1150 cm$^{-1}$.

EXAMPLE 4

((−)-2-butoxypropionic acid)

15.5 g of (−)-ethyl-2-butoxy-propionate produced in the same manner as in Example 1 was added dropwise into 40 ml of 5M-NaOH aqueous solution and the mixture was stirred at room temperature for 4 hours. Then, the mixture was made acidic by adding 20 g of $H_2SO_4$ and subjected to extraction with ether. The ether was distilled off from the extract, which was then dried with anhydrous $Na_2SO_4$. The product showed an optical rotation $[\alpha]_D^{25°}$ of −74° and gave an IR spectrum (KBr disk method) as shown in FIG. 1 with characteristic absorption peaks at 3100, 2960, 2650, 2550, 1720 and 1130 cm$^{-1}$.

EXAMPLE 5

((−)-2-heptyloxypropionic acid)

15.1 g of (−)-ethyl-2-heptoxy-propionate produced in the same manner as in Example 2 was added dropwise into 40 ml of 3.8M-NaOH aqueous solution and the mixture was stirred at room temperature for 10 hours. Then, 7.5 g of concentrated sulfuric acid was added and the mixture was subjected to extraction with ether. The extract was dried with anhydrous $Na_2SO_4$ and the ether was distilled off. The optical rotation and IR peaks of the product were as follows:
$[\alpha]_D^{24°} = -61°$, IR: 2940, 1730, 1130 cm$^{-1}$.

EXAMPLE 6

((−)-ethyl-2-octadecyloxypropionate)

60.5 g of L-(+)-ethyl lactate and 95.4 g of 1-iodooctadecane were mixed, and 71.7 g of freshly prepared $Ag_2O$ was added in 30 minutes. The mixture was held at 40°–50° C. under stirring for 8 hours, left standing at room temperature for about 100 hours, then diluted with about 300 ml of ether, filtrated and subjected to distillation for removing the ether. The residue was washed with 100 ml of 5% aqueous KOH solution, dried with anhydrous $Na_2SO_4$ and recrystallized for purification to obtain 20.5 g of (−)-ethyl-2-octadecyloxypropionate was obtained. The optical rotation and IR peaks of the product were as follows:
$[\alpha]_D^{25°} = -$IR: 2930, 2850, 1755, 1140 cm$^{-1}$.

EXAMPLE 7

((−)-ethyl-2-decyloxypropionate)

47.4 g of L−+(.)-ethyl lactate and 93.9 g of 1-iododecane were mixed, and 60.1 g of freshly prepared $Ag_2O$ was added in about 1.5 hours. The mixture was held at 40°–50° C. under stirring, left standing at room temperature for 24 hours, then diluted with 350 ml of ether, filtrated and subjected to distillation for removing the ether. The residue was washed with about 100 ml of 5% aqueous KOH solution, dried with anhydrous $Na_2SO_4$ and subjected to reduced-pressure distillation to collect a fraction at 141°–146° C./5 mmHg, whereby 13.6 g of (−)-ethyl-2-decyloxypropionate was obtained.

The optical rotation and IR peaks of the product were as follows:

[α]$_D^{23°}$ = −48°, IR: 2920, 2850, 1750, 1150 cm$^{-1}$.

EXAMPLE 8

(4'-hexyl-4-α-butoxypropanoyloxyazobenzene)

30.1 g (0.17 M) of 4-hexylaniline was cooled to 0° C. or below, 85 g of 10% aqueous hydrochloric acid solution was added, and then a solution of 11.6 g of sodium nitrite in 68 g of water was added. During the addition, the mixture was cooled so as not to exceed 0° C. After the addition, the mixture was allowed to react for 30 minutes, transferred into a dropping funnel and added dropwise into 170 g of an 8% NaOH aqueous solution containing 16 g of phenol held at 5° C. or below. After the addition, the mixture was stirred for 0.5 hour, and then 10% hydrochloric acid aqueous solution was added thereto until a pH of 5–6 to precipitate the reaction product. The precipitate was separated by filtration, washed with water and dried overnight under reduced pressure. After the drying, the product was washed with 500 ml of petroleum ether and further dried under reduced pressure to obtain 29.6 g (0.10M) of 4-hydroxy-4'-hexylazobenzene. The yield was 59%.

2.4 g of (−)-2-butoxypropionic acid was charged in a flask and 2.5 g of thionyl chloride was gradually added thereto to allow a reaction for 30 minutes followed by removal of thionyl chloride by distillation. The thus obtained 2-butoxypropionic acid chloride was added to a mixture of 3.0 g of the 4-hydroxy-4'-hexylazobenzene and 20 ml of dry pyridine. The mixture was allowed to react for about 20 hours at room temperature and charged into deionized water for cooling. The resultant precipitate was separated by filtration, recrystallized in ethanol and dried under vacuum to obtain 1.1 g of 4'-hexyl-4-α-butoxypropanoyloxyazobenzene. The product showed the following properties:

Phase transition temperature: Cryst. $\underset{36.9° C.}{\overset{46.5° C.}{\rightleftarrows}}$ Iso.

IR: 2940, 1775, 1600, 1500, 1200, 1140, 840 cm$^{-1}$.

EXAMPLE 9

(4-heptyl-4-a-butoxypropanoyloxyazobenzene) 32.9 g (0.17M) of 4-heptylaniline was cooled to 0° C. or below, 85 g of 10% aqueous hydrochloric acid solution was added, and then a solution of 12.1 g of sodium nitrite in 70 ml of water was added. During the addition, the mixture was cooled so as not to exceed 0° C. After the addition, the mixture was allowed to react for 30 minutes, transferred into a dropping funnel and added dropwise into 300 ml of an 8% NaOH aqueous solution containing 16 g of phenol held at 5° C. or below. After the addition, the mixture was stirred for 1 hour, and then 10% hydrochloric acid aqueous solution was added thereto until a pH of 5–6 to precipitate the reaction product. The precipitate was separated by filtration, washed with water and dried overnight under reduced pressure. After the drying, the product was washed with 500 ml of petroleum ether and further dried under reduced pressure to obtain 34.7 g (0.12M) of 4-hydroxy-4'-heptylazobenzene. The yield was 71%.

2.4 g of (−)-2-butoxypropionic acid was charged in a flask and 2.5 g of thionyl chloride was gradually added thereto to allow a reaction for 30 minutes followed by removal of thionyl chloride by distillation. The thus obtained 2-butoxypropionic acid chloride was added to a mixture of 3.2 g of the 4-hydroxy-4'-heptylazaobenzene and 20 mg of dry pyridine. The mixture was allowed to react for about 5 hours at room temperature and charged into deionized water for cooling. The resultant precipitate was separated by filtration, recrystallized in ethanol and further purified by a silica gel column chromatography with benzene as the solvent to obtain 1.2 g of 4'-heptyl-4-α-butoxypropanoyloxyazobenzene. The product showed the following properties:

Phase transition temp.: Cryst. $\underset{39.6° C.}{\overset{52.0° C.}{\rightleftarrows}}$ Iso.

IR: 2930, 1775, 1600, 1500, 1205, 1140, 840 cm$^{-1}$

The IR spectrum (KBr disk method) of the products is shown in FIG. 2.

EXAMPLE 10

(4''-octyl-4-α-butoxypropanoyloxyazobenzene)

35 g (0.17M) of 4-octylaniline was cooled to 0° C. or below, 85 g of 10% aqueous hydrochloric acid solution was added, and then a solution of 12.0 g of sodium nitrite in 68 ml of water was added. During the addition, the mixture was cooled so as not to exceed 0° C. After the addition, the mixture was allowed to react for 30 minutes, transferred into a dropping funnel and added dropwise into 170 g of an 8% NaOH aqueous solution containing 16 g of phenol held at 5° C. or below. After the addition, the mixture was stirred for 1 hour, and then 10% hydrochloric acid aqueous solution was added thereto until a pH of 5–6 to precipitate the reaction product. The precipitate was separated by filtration, washed with water and dried overnight under reduced pressure. After the drying, the product was washed with 500 ml of petroleum ether and further dried under reduced pressure to obtain 30.8 g (0.10M) of 4-hydroxy-4'-octylazobenzene. The yield was 59%.

Into a solution of 5 g of KOH in 50 ml of ethanol, 12.4 g of 4-hydroxy-4'-octylazobenzene was charged and allowed to react for 6 hours. The ethanol was distilled off, and the precipitated crystal was washed with acetone and dried under reduced pressure to obtain 8.8 g of potassium-4'-octyl-4-hydroxyazobenzene.

2.8 g of thionyl chloride was gradually added dropwise to 2.1 g of (−)-2-butoxypropionic acid. The mixture was allowed to react for 30 minutes at room temperature and then thionyl chloride was distilled off. The thus obtained 2-butoxypropionic acid chloride was added dropwise to a mixture of 3.6 g of potassium4'-octyl-4-hydroxyazobenzene, 16 ml of acetone and 0.84 g of NaHCO$_3$. After the addition, deionized water was added to cause precipitation. The precipitate was separated by filtration and recrystallized in ethanol to obtain 1.8 g of 4'-octyl-4-α-butoxypropanoyloxyazobenzene. The product showed the following properties:

Phase transition temperature: Cryst. $\underset{31.3° C.}{\overset{49.5° C.}{\rightleftarrows}}$ Iso.

IR: 2930, 1775, 1600, 1500, 1205, 1140, 840 cm$^{-1}$.

EXAMPLE 11

(4'-hexyloxy-4-α-butoxypropanoyloxyazobenzene)

Into a cooled mixture of 16.5 g of n-hexyloxyaniline and 50 ml of deionized water, 43 g of 10% hydrochloric acid aqueous solution was added. Then, a solution of 5.9 g of NaN02 in 34 ml of water was added dropwise under cooling. The resultant reaction product was added into a solution of 8.0 g of phenol in 86.6 g of 8% NaOH aqueous solution. During the addition the mixture was held at 5° C. or below. After the addition, the mixture was left standing for 1 hour, and then 10% hydrochloric acid aqueous solution was added thereto until a pH of 1 to precipitate the reaction product. The precipitated microcrystal was separated by filtration and dried under reduced pressure. After the drying, the product was washed with petroleum ether and further dried under reduced pressure to obtain 12.1 g of 4-hydroxy-4'-hexyloxyazobenzene.

2.4 g of (—)-2-butoxypropionic acid was charged in a flask and 2.5 g of thionyl chloride was gradually added thereto to allow a reaction for 30 minutes followed by removal of thionyl chloride by distillation. The thus obtained 2-butoxypropionic acid chloride was added to a mixture of 3.2 g of the 4-hydroxy-4'-hexyloxyazobenzene and 20 ml of dry pyridine stirred in a flask. The mixture was allowed to stand for about 20 hours at room temperature and charged into deionized water for cooling. The resultant precipitate was separated by filtration, and further purified by a silica gel column chromatography with benzene as the solvent to obtain 2.0 g of 4'-hexyloxy-4-α-butoxypropanoyloxyazobenzene. The product showed the following properties:

Phase transition temp.: Cryst. $\underset{61.1° C.}{\overset{72.5° C.}{\rightleftarrows}}$ Iso.

IR: 2940, 1760, 1600, 1490, 1200, 1130, 840 cm$^{-1}$.

EXAMPLE 12

(4'-octyl-4-α-heptyloxypropanoyloxyazobenzene)

35 g (0.17M) of 4-octylaniline was cooled to 0° C. or below, 85 g of 10% aqueous hydrochloride acid solution was added, and then a solution of 12.0 g of sodium nitrite in 68 ml of water was added. During the addition, the mixture was cooled so as not to exceed 0° C. After the addition, the mixture was allowed to react for 30 minutes, transferred into a dropping funnel and added dropwise into 170 g of an 8% NaOH aqueous solution containing 16 g of phenol held at 5° C. or below. After the addition, the mixture was stirred for 1 hour, and then 10% hydrochloric acid aqueous solution was added thereto until a pH of 5-6 to precipitate the reaction product. The precipitate was separated by filtration, washed with water, overnight under reduced pressure. After the drying, the product was washed with 500 ml of petroleum ether and further dried under reduced pressure to obtain 30.8 g (0.10M) of 4-hydroxy-4'-octylazobenzene. The yield was 59%.

3.8 g of (—)-2-heptyloxypropionic acid was charged in a flask and 3.6 g of thionyl chloride was added thereto to allow a reaction for 30 minutes followed by removal of thionyl chloride by distillation. The thus obtained 2-heptyloxypropionic acid chloride was added to a mixture of 5.3 g of 4'-potassiumoxy-4-octylazobenzene, 20 ml of acetone and 1.3 g of NaHCO$_3$. After the addition, the mixture was allowed to react for 1 hour, and 20 ml of water was added to separate an oil layer. The oil layer was cooled to form a solid, which was then separated by filtration and purified with a silica gel column chromatography with benzene as the solvent to obtain 3.1 g of 4'-octyl-4-α-heptyloxypropanoyloxyazobenzene. The product showed the following properties:

Phase transition temp.: Cryst. $\underset{29.8° C.}{\overset{42.1° C.}{\rightleftarrows}}$ Iso.

IR: 2930, 1780, 1600, 1500, 1200, 1110, 840 cm$^{-1}$.

Figure 3:
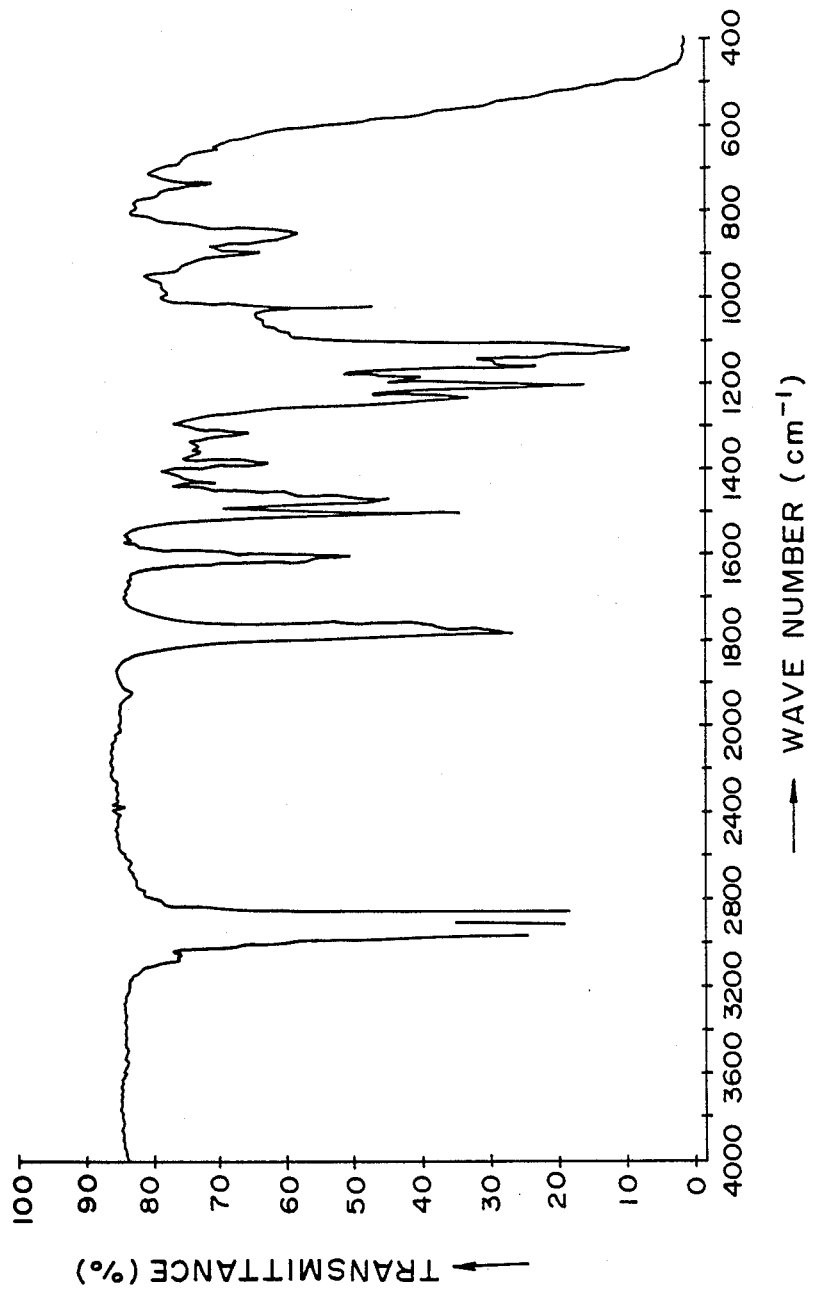

The IR spectrum (bulk method) of the product is shown in FIG. 3.

EXAMPLE 13

(4'-hexyloxy-4-α-heptyloxypropanoyloxyazobenzene)

Into a cooled mixture of 16.5 g of n-hexyloxyaniline and 50 ml of deionized water, 43 g of 10% hydrochloric acid aqueous solution was added. Then, a solution of 5.9 g of NaNO$_2$ in 34 ml of water was added dropwise under cooling. The resultant reaction product was added into a solution of 8.0 g of phenol in 86.6 g of 8% NaOH aqueous solution. During the addition the mixture was held at 5° C. or below. After the addition, the mixture was left standing for 1 hour, and then 10% hydrochloric acid aqueous solution was added thereto until a pH of 1 to precipitate the reaction product. The precipitated microcrystal was separated by filtration and dried under reduced pressure. After the drying, the product was washed with petroleum ether and further dried under reduced pressure to obtain 12.1 g of 4-hydroxy-4'-hexyloxyazobenzene.

3.8 g of (—)-2-heptyloxypropionic acid was charged in a flask and 3.6 g of thionyl chloride was gradually added thereto to allow a reaction for 30 minutes followed by removal of thionyl chloride by distillation. The thus obtained 2-heptyloxypropionic acid chloride was added to a mixture of 4.5 g of the 4-hydroxy-4'-hexyloxyazobenzene and 20 ml of dry pyridine stirred in a flask. The mixture was allowed to react for about 5 hours at room temperature and charged into deionized water for cooling. The resultant precipitate was separated by filtration, and purified by a silica gel column chromatography with benzene as the solvent to obtain 2.8 g of 4'-hexyloxy-4-α-heptyloxypropanoyloxyazobenzene. The product showed the following properties:

Phase transition temp.: Cryst. $\overset{69.1° C.}{\longrightarrow}$ Iso.
$56.7° C. \searrow \quad \nearrow 71.1° C.$
Ch.

IR: 2940, 1760, 1600, 1500, 1210, 1130, 845 cm$^{-1}$.

EXAMPLE 14

(4'-hexyloxy-4-α-butoxypropanoyloxyazoxybenzene)

Into a cooled mixture of 16.5 g of n-hexyloxyaniline and 50 ml of deionized water, 43 g of 10% hydrochloric acid aqueous solution was added. Then, a solution of 5.9 g of NaNO$_2$ in 34 ml of water was added dropwise under cooling. The resultant reaction product was added into a solution of 8.0 g of phenol in 86.6 g of 8%

NaOH aqueous solution. During the addition the mixture was held at 5° C. or below. After the addition, the mixture was left standing for 1 hour, and then 10% hydrochloric acid aqueous solution was added thereto until a pH of 1 to precipitate the reaction product. The precipitated microcrystal was separated by filtration and dried under reduced pressure. After the drying, the product was washed with petroleum ether and further dried under reduced pressure to obtain 12.1 g of 4-hydroxy-4'-hexyloxyazobenzene.

2.4 g of (−)-2-butoxypropionic acid was charged in a flask and 2.5 g of thionyl chloride was gradually added thereto to allow a reaction for 30 minutes followed by removal of thionyl chloride by distillation. The thus obtained 2-butoxypropionic acid chloride was added to a mixture of 3.2 g of the 4-hydroxy-4'-hexyloxyazobenzene and 20 ml of dry pyridine stirred in a flask. The mixture was allowed to stand for 20 hours at room temperature and charged into deionized water for cooling. The resultant precipitate was separated by filtration, and purified by a silica gel column chromatography with benzene as the solvent to obtain 2.0 g of 4'-hexyloxy-4-α-butoxypropanoyloxyazobenzene having a melting point of 72.5° C.

0.81 g of the 4'-hexyloxy-4-α-butoxypropanoyloxyazobenzene. was dissolved in 40 ml of glacial acetic acid and the mixture was stirred under heating at 50°-60° C. About 5 ml of 31% H$_2$O$_2$ aqueous solution was added dropwise to the mixture in about 6 hours. The mixture was further left standing for 4 hours at 50°-60° C., for 30 hours at room temperature, charged into 400 ml of deionized water and extracted with ether. The extract was washed with 50 ml of 5% Na$_2$CO$_3$ aqueous solution and deionized water, and then dried with anhydrous Na$_2$SO$_4$. After distilling off ether; the resultant yellow crystal was recrystallized in ethanol to obtain 0.3 g of 4'-hexyloxy-4-α-butoxypropanoyloxy azoxybenzene showing the following properties:

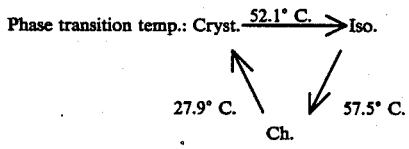

IR: 2930, 1760, 1600, 1500, 1460, 1260, 1130, 840 cm$^{-1}$.

EXAMPLE 15

(4'-octyl-4-α-heptyloxypropanoyloxyazoxybenzene)

35 g (0.17M) of 4-octylaniline was cooled to 0° C. or below, 85 g of 10% aqueous hydrochloric acid solution was added, and then a solution of 12.0 g of sodium nitrite in 68 ml of water was added. During the addition, the mixture was cooled so as not to exceed 0° C. After the addition, the mixture was allowed to react for 30 minutes, transferred into a dropping funnel and added dropwise into 170 g of an 8% NaOH aqueous solution containing 16 g of phenol held at 5° C. or below. After the addition, the mixture was stirred for 1 hour, and then 10% hydrochloric acid aqueous solution was added thereto until a pH of 5-6 to precipitate the reaction product. The precipitate was separated by filtration, washed with water, overnight under reduced pressure. After the drying, the product was washed with 500 ml of petroleum ether and further dried under reduced pressure to obtain 30.8 g (0.10M) of 4-hydroxy-4'-octylazobenzene. The yield was 59%.

3.8 g of (−)-2-heptyloxypropionic acid was charged in a flask and 3.6 g of thionyl chloride was added thereto to allow a reaction for 30 minutes followed by removal of thionyl chloride by distillation. The thus obtained 2-heptyloxypropionic acid chloride was added to a mixture of 5.3 g of 4'-potassiumoxy-4-octylazobenzene, 20 ml of acetone and 1.3 g of NaHCO$_3$. After the addition, the mixture was allowed to react for 1 hour, and 20 ml of water was added to separate an oil layer. The oil layer was cooled to form a solid, which was then separated by filtration and purified with a silica gel column chromatography with benzene as the solvent to obtain 3.1 g of 4'-octyl-4-α-heptyloxypropanoyloxyazobenzene having a melting point of 42.1° C.

0.8 g of the 4'-octyl-4-α-heptyloxypropanoyloxyazobenzene was dissolved in 50 ml of glacial acetic acid and the mixture was stirred under heating at 50°-60° C. 7 ml of 31% H$_2$O$_2$ aqueous solution was added dropwise to the mixture in about 1.5 hours. The mixture was left standing for 22 hours at 50°-60° C., charged into 500 ml of deionized water and extracted with ether. The extract was washed with 50 ml of 5% Na$_2$CO$_3$ aqueous solution and 100 ml deionized water. After distilling off ether; the product was purified with a silica gel chromatography with benzene as the solvent to obtain 0.3 g of 4'-octyl-4-α-heptyloxypropanoyloxyazobenzene showing the following properties:

Phase transition temp.: Cryst. $\underset{5.5° C.}{\overset{39.2° C.}{\rightleftarrows}}$ Iso.

IR: 2920, 1775, 1600, 1500, 1465, 1200, 1120, 830 cm$^{-1}$.

EXAMPLE 16

(4'-hexyloxy-4-α-heptyloxypropanoyloxyazoxybenzene)

Into a cooled mixture of 16.5 g of n-hexyloxyalinine and 50 ml of deionized water, 43 g of 10% hydrochloric acid aqueous solution was added. Then, a solution of 5.9 g of NaNO$_2$ in 34 ml of water was added dropwise under cooling. The resultant reaction product was added into a solution of 8.0 g of phenol in 86.6 g of 8% NaOH aqueous solution. During the addition the mixture was held at 5° C. or below. After the addition, the mixture was left standing for 1 hour, and then 10% hydrochloric acid aqueous solution was added thereto until a pH of 1 to precipitate the reaction product. The precipitated microcrystal was separated by filtration and dried under reduced pressure. After the drying, the product was washed with petroleum ether and further dried under reduced pressure to obtain 12.1 g of 4-hydroxy-4'-hexyoxyazobenzene.

3.8 g of (−)-2-heptyloxypropionic acid was charged in a flask and 3.6 g of thionyl chloride was added thereto to allow a reaction for 30 minutes followed by removal of thionyl chloride by distillation. The thus obtained 2-heptyloxypropionic acid chloride was added to a mixture of 4.5 g of the 4-hydroxy-4'-hexyloxyazobenzene and 20 ml of dry pyridine stirred in a flask. The mixture was allowed to stand for 20 hours at room temperature and charged into deionized water for cooling. The resultant precipitate was separated by filtration, and purified by a silica gel column chromatography with benzene as the solvent to obtain 2.8 g of 4'-hexyloxy-4-α-heptyloxypropanoyloxyazobenzene having a melting point of 69° C.

0.82 g of the 4'-hexyloxy-4-α-heptyloxypropanoyloxyazobenzene was dissolved in 55 ml of glacial acetic acid and the mixture was held at 50°–60° C. 7 ml of 31% $H_2O_2$ aqueous solution was added dropwise to the mixture in about 1 hour. The mixture was left standing for 24 hours at 50°–60° C., further for 24 hours at room temperature, charged into 800 ml of deionized water and extracted with ether. The extract was washed with 100 ml of aqueous solution containing 3.3 g of $Na_2CO_3$ and 100 ml of deionized water, and then dried with anhydrous $Na_2SO_4$. After distilling off ether; the product was purified with a silica gel chromatography with benzene as the solvent to obtain 0.3 g of 4'-hexyloxy-4-α-heptyloxypropanoyloxyazobenzene showing the following properties:

Phase transition temp.: Cryst. $\underset{\xleftarrow{10.4° C.}}{\xrightarrow{50.8° C.}}$ Iso.

IR: 2940, 1760, 1600, 1500, 1470, 1200, 1140, 840 $cm^{-1}$.

EXAMPLE 17

(5-decyl-2-(4'-α-pentyloxypropanoyloxyphenylpyrimidine)

40 g of p-hydroxybenzonitrile was dissolved in a mixture of 100 ml of ethanol and 125 ml of benzene. The solution was saturated with dry HCl and left standing for 1–2 days at room temperature. The solution was diluted with ether to precipitate a crystal, which was then separated by filtration to remove ether. Ammonia-saturated ethanol was added thereto, and the mixture was left standing for 1–2 days. Then, ether was added to the mixture to cause recrystallization to 4-hydroxybenzamidine hydrochloride. 9 g of the 4-hydroxybenzamidine hydrochloride and 12 g of α-decyl-β-dimethylaminoacrolein were added into anhydrous methanol containing 3.0 g of metallic sodium, and the mixture was refluxed for 10 hours. After distilling off the methanol, the product was charged in dilute acetic acid and extracted with ether. The extract was purified with a silica gel column chromatography to obtain 5-decyl-2-(4-hydroxyphenyl)pyrimidine.

10 ml of thionyl chloride was added to 2.0 g of α-pentyloxypropionic acid and the mixture was refluxed under heat for 2 hours. Excess of thionyl chloride was distilled off to obtain α-pentyloxypropionic acid chloride. 20 ml of dry pyridine was added thereto, and 7.0 g of 5-decyl-2-(4-hydroxyphenyl)pyrimidine dissolved in 50 ml of dry benzene was further added dropwise. After the addition, the mixture was refluxed under heat, charged into ice water and extracted with benzene. The extract was purified with a silica gel column chromatography to obtain 5-decyl-2-(4'-α-pentyloxypropanoyloxyphenyl)pyrimidine.

EXAMPLE 18

(4'-α-dodecyloxypropanoyloxybiphenyl ester of 4-octyloxybenzoic acid)

10 ml of thionyl chloride was added to 2.0 g of α-dodecyloxypropionic acid, and the mixture was refluxed under heat for 2 hours. Excess of thionyl chloride was distilled off to obtain α-dodecyloxypropionic acid chloride. 20 ml of dry pyridine was added thereto, and 5.0 g of 4,4'-dihydroxybiphenyl was further added dropwise. After the addition, the mixture was refluxed under heat for 3 hours, charged into ice water, and extracted with benzene. The extract was purified with a silica gel column chromatography to obtain 4-hydroxy-4'-α-dodecyloxypropanoyloxybiphenyl.

40 ml of thionyl chloride was added to 2.0 g of p-octyloxybenzoic acid, and the mixture was refluxed under heat for 2 hours. Then, excess of thionyl chloride was distilled off to obtain p-octyloxybenzoic acid chloride. 20 ml of dry pyridine was added thereto, and the 4-hydroxy-4'-α-dodecyloxypropanoyloxybiphenyl dissolved in 40 ml of dry benzene was further added. The mixture was then refluxed for 5 hours, charged into ice water, and extracted with ether. The extract was purified with a silica gel column chromatography to obtain 4'-α-dodecyloxypropanoyloxybiphenyl ester of 4-octyloxybenzoic acid.

EXAMPLE 19

(4'-(4''-α-octyloxypropanoyloxybenzoyloxy)phenyl ester of 4-octyloxybiphenylcarboxylic acid)

40 ml of thionyl chloride was added to 5.0 g of 4-octyloxybiphenylcarboxylic acid and the mixture was refluxed under heat for 3 hours. Excess of thionyl chloride was distilled off to obtain 4-octyloxybiphenylcarboxylic acid chloride, which was then added to a solution of 5.0 g of hydroquinone in 50 ml of pyridine. After 2 hours of reaction, the mixture was refluxed under heat for 10 hours, charged into ice water, and extracted with benzene. The extract was purified with a silica gel column chromatography to obtain 4-hydroxyphenyl ester of 4-octyloxybiphenylcarboxylic acid.

10 ml of thionyl chloride was added to 2.0 g of α-octyloxypropionic acid, and the mixture was refluxed under heat for 2 hours. Then, excess thionyl chloride was distilled off to obtain α-octyloxypropionic acid chloride. 20 ml of dry pyridine was added thereto, and a solution of 5.0 g of p-hydroxybenzoic acid dissolved in 40 ml of dry pyridine was further added. After the addition, the mixture was refluxed for 2 hours, charged into ice water, and extracted with benzene. The extract was purified with a silica gel column chromatography to obtain 4-α-octyloxypropanoyloxybenzoic acid.

2.0 g of 4-α-octyloxypropanoyloxybenzoic acid and 2.5 g of 4'-hydroxyphenyl ester of 4-octyloxybiphenylcarboxylic acid were added to 50 g of polyphosphoric acid and reacted for 10 hours at 100° C. The reaction product was charged into ice water, extracted with benzene, and recrystallized in ethanol to obtain 4'-(4''-α-octyloxypropanoyloxybenzoyloxy)phenyl ester of 4-octyloxybiphenylcarboxylic acid.

EXAMPLE 20

(Property of liquid crystal composition containing a mesomorphic compound prepared in Example 12)

A liquid crystal composition composed of 88 wt. % of DOBAMBC and 12 wt. % of the mesomorphic compound prepared in Example 12 was found to show SmC* at a lowered temperature range of 47° C. to 80° C.

EXAMPLE 21

(Property of liquid crystal composition containing a mesomorphic compound prepared in Example 15)

A liquid crystal composition as shown in the following Table 3 was prepared and found to show SmC* at a temperature range of 40° C. to 5° C. during the course of cooling.

TABLE 3

| Structure | wt. % |
|---|---|
| $C_8H_{17}O-\bigcirc-\overset{O}{\underset{\|}{C}}-O-\bigcirc-OCH_2\overset{*}{\underset{CH_3}{C}}HC_2H_5$ | 60 wt. % |
| $C_8H_{17}O-\bigcirc-O-\overset{O}{\underset{\|}{C}}-\bigcirc-\bigcirc-CH_2\overset{*}{\underset{CH_3}{C}}HC_2H_5$ | 30 wt. % |
| $C_8H_{17}-\bigcirc-\underset{O}{N=N}-\bigcirc-O\overset{O}{\underset{\|}{C}}\overset{*}{\underset{CH_3}{C}}HOC_7H_{15}$ | 10 wt. % |

EXAMPLE 22

(Property of liquid crystal composition containing a mesomorphic compound prepared in Example 12) A liquid crystal composition composed of 98 wt. % of DOBAMBC and 2 wt. % of the mesomorphic compound prepared in Example 12 was found to show a spontaneous polarization twice as large as that of MBRA 8 alone.

| | |
|---|---|
| MBRA 8 alone | Ps = 34.6 μc/m² (Tc-T = 21.8° C.) |
| Example 22 | Ps = 60.1 μc/m² (Tc-T = 18.2° C.) |

The spontaneous polarization was determined by measuring a polarization inversion current. (Reference: Preprint for Year 1983, 9th Liquid Crystal Forum, pp 82, Miyazato, Takezoe, Fukuda et al.)

EXAMPLE 23

((+)-2-butoxypropanol)

2.0 g of LiAlH$_4$ was added to 62 ml of ether and the mixture was stirred for 3 hours. To the mixture was added dropwise 12.7 g of (−)-ethyl-2-butoxypropionate in the same manner as in Example 1, and the mixture was stirred for 15 minutes. Then, 50 ml of water and 50 ml of 10% H$_2$SO$_4$ aqueous solution were added thereto. The ther layer was separated, dried with MgSO$_4$ and filtrated. Ether was distilled off to obtain the objective product at an yield of 7.4 g. The optical rotation $[\alpha]_D^{24°}$ was +24.4°.

EXAMPLE 24

((+)-2-heptyloxypropanol)

2.0 g of LiAlH$_4$ was added to 62 ml of ether and the mixture was stirred for 3 hours. To the mixture wa added dropwise 14.6 g of (−)-ethyl-2-heptyloxypropionate in the same manner as in Example 2, and the mixture was stirred for 15 minutes. Then, a small amount of water and then 50 ml of 10% H$_2$SO$_4$ aqueous solution were added thereto. The ether layer was separated, dried with MgSO$_4$ and filtrated. Ether was distilled off to obtain the objective product at an yield of 9.0 g. The optical rotation $[\alpha]_D^{25°}$ was +17.4°

EXAMPLE 25

((+)-2-decyloxypropanol)

2.2 g of LiAlH$_4$ was added to 80 ml of ether and the mixture was stirred for 5 hours. To the mixture was added dropwise 13.6 g of (−)-ethyl-2-decyloxypropionate in the same manner as in Example 7, and the mixture was stirred for 15 minutes. Then, 50 ml of water and further 50 ml of 5% H$_2$SO$_4$ aqueous solution were added thereto. The ether layer was separated, dried with MgSO$_4$ and filtrated. Ether was distilled off and the residue was subjected to distillation under reduced pressure, whereby 6.9 g of (+)-2-decyloxypropanol was obtained by collecting a fraction of 94°–96° C./1 mmHg.

The product showed the following properties:
$[\alpha]_D^{24°} = +16.1°$
IR: 3430, 2925, 2850, 1470, 1380, 1100, 1050 cm$^{-1}$.
$^1$H-NMR: 3.3–3.7 ppm, 2.2–2.3 ppm, 0.8–1.3 ppm.

EXAMPLE 26

((+)-2-dodecyloxypropanol)

1.9 g of LiAlH$_4$ was added to 70 ml of ether and the mixture was stirred for 4 hours. To the mixture was added dropwise 16.9 g of (−)-ethyl-2-dodecyloxypropionate in the same manner as in Example 3, and the mixture was stirred for 15 minutes. Then, 50 ml of deionized water and further 50 ml of 10% H$_2$SO$_4$ aqueous solution were added thereto. The ether layer was separated, dried with MgSO$_4$ and filtrated. Ether was distilled off to obtain the objective product at an yield of 12.0 g. The product showed the following properties:
$[\alpha]_D^{26°} = +11.1°$.
IR: 3430, 2930, 2850, 1470, 1380, 1100, 1050 cm$^{-1}$.

EXAMPLE 27

((+)-2-octadecyloxypropanol)

4.5 g of LiAlH$_4$ was added to 150 ml of ether and the mixture was stirred for 3.5 hours. To the mixture was added dropwise 38.8 g of (−)-ethyl-2-octadecyloxypropionate in the same manner as in Example 6, and the mixture was stirred for 20 minutes. Then, 50 ml of water was added thereto and 10% H$_2$SO$_4$ aqueous solution was further added to give a pH of 7–8. The ether layer was separated, dried with MgSO$_4$ and filtrated. Ether was distilled off and the residue was subjected to distillation under reduced pressure, whereby 14.0 g of (+)-2-octadecyloxypropanol was obtained by collecting a fraction of 175°–179° C./0.9 mmHg.

The product showed the following properties:
$^1$H-NMR 3.3–3.6 ppm, 2.0–2.2 ppm,
0.9–1.7 ppm
$[\alpha]_D^{28°} = 12.2°$
IR: 3380, 2910, 2850, 1465, 1375, 1095, 1045 cm$^{-1}$

EXAMPLE 28

(heptyloxypropyl 4′-octyloxybiphenyl-4-carboxylate)

85 g of 4-oxybiphenyl was dissolved in 1.5 l of 1.5N-NaOH solution and reacted with 2 mols of methyl sulfate while the temperature being suppressed not to exceed 60° C. The system was then raised in temperature to 70° C. in 30 minutes. The product was recrystallized in ethanol to obtain 4-methoxybiphenyl crystal having a melting point of 80.5° C. at an yield of 90–95%.

11.5 g of 4-methoxybiphenyl was dissolved in 75 ml of carbon disulfide just after distillation, then cooled to 0°-2° C., and 9.5 g of anhydrous aluminum chloride was quickly added thereto under stirring. Then, 5.8 ml of acetyl chloride was added dropwise in 5-10 minutes. The temperature was gradually raised to 35° C. to complete the reaction. After about 45 minutes of reflux, 60 ml of cooled conc. hydrochloric acid was added to cause decomposition. After blowing steam into the mixture to remove the solvent, the mixture was rapidly cooled under sufficient stirring to result in brownish pink crystal. In order to remove a 3-ketone isomer, the mixture was subjected to two times of extraction with 40 ml of ether and then recrystallized in isopropyl alcohol to obtain 4-acetyl-4'-methoxybiphenyl having a melting point of 156.5° C. at a yield of 60-77%.

18 g of 4-acetyl-4'-methoxybiphenyl was dissolved in 285 ml of dioxane and oxidized with a dilute sodium hypobromite. The product was recrystallized in a mixture of ethanol and acetic acid to obtain 4'-methoxybiphenyl-4-carboxylic acid.

A mixture of 25 of 4-methoxybiphenyl-4-carboxylic acid, 1 1 of acetic acid and 200 ml of 48% bromic acid was refluxed for 12-14 hours and then thrown into 2.5 l of water. After cooling, the resultant crystal was collected to obtain 4'-hydroxybiphenylcarboxylic acid.

0.01 mol of 4'-hydroxybiphenylcarboxylic acid and 0.02 mol of potassium hydroxide were dissolved in a mixture of 300 ml of alcohol and 30 ml of water. Then, 1.2 ml of n-octyl bromide was added thereto, and the resultant mixture was refluxed for 12 hours. A 10% potassium hydroxide solution containing 1.12 g of KOH was added and the resultant mixture was refluxed for 2 hours to cause hydrolysis. The product was recrystallized in a mixture of ethanol and glacial acetic acid to obtain 4'-n-octyloxybiphenyl carboxylic acid.

1.0 g of 4'-n-octyl oxybiphenylcarboxylic acid was charged in a 4-necked flask, and 40 ml of thionyl chloride (SOCl$_2$) was added thereto. The mixture was stirred and refluxed under heat for 4 hours. After stopping the heating, the mixture was stirred for 7 hours, and SOCl$_2$ was distilled off. After the complete removal, 40 ml of dry pyridine was added, and a solution of 2.1 g of (+)-2-heptyloxypropanol in 40 ml of dry benzene was added in 40 minutes. The mixture was left standing at room temperature for 15 hours and refluxed under heat for 3 hours. After distilling off the solvent, the residue was dissolved in benzene and subjected to a silica gel column chromatography with benzene as the solvent to obtain 0.7 g of 2'-heptyloxybenzenepropyloctyloxybiphenyl- 4-carboxylate, which was recrystallized in ethanol.

The following properties were observed.

DSC: Showing a liquid crystal phase in a range of 23°-39° C.

IR: 2930, 2850, 1720, 1600, 1290, 1120, 830, 770 cm$^{-1}$ $^1$H-NMR: 7.0-8.1 ppm, 3.5-4.3 ppm, 0.9-1.5 ppm.

EXAMPLE 29

(butoxypropyl-4'-octyloxybiphenyl-4-carboxylate)

1.0 g of 4'-n-octyloxybiphenylcarboxylic acid prepared in the same manner as in Example 28 was charged in a 4-necked flask, and 40 ml of thionyl chloride was added thereto. The mixture. was stirred and refluxed under heat for 4 hours. After stopping the heating, the mixture was stirred for 7 hours, and thionyl chloride was distilled off. After the complete removal, 40 ml of dry pyridine was added, and a solution of 1.0 g of (+)-2-butoxypropanol in 36 ml of dry benzene was added dropwise in 30 minutes. The mixture was left standing at room temperature for 19 hours. After distilling off the solvent, the residue was dissolved in benzene and subjected to a silica gel column chromatography with benzene as the solvent to obtain 0.5 g of 2'-butoxypropyloctyloxybiphenyl-4-carboxylate.

The following properties were observed.

DSC: Showing a monotropic liquid crystal phase in a range of 34°-36° C.

IR: 2930, 2850, 1720, 1600, 1290, 1270, 1120, 830, 770 cm$^1$

EXAMPLE 30

(4-(5-(4'-butylphenyl)pyrimidine-2-yl)benzoic acid 2'-dodecyloxypropyl ester)

A mixture of 30 g of 2-(4-butylphenyl)malondialdehyde tetraethyl acetal, 40 ml of ethanol, 3.6 ml of water and 3 drops of conc. sulfuric acid was stirred for 18 hours at 50° C. and diluted with ether. After nonreacted 2-(4-butylphenyl)malondialdehyde tetraethyl acetal was removed by dil. Na$_2$CO$_3$ aqueous solution, ether was distilled off. 15 g of the thus obtained 2-(4-butyl)-3-ethoxyacrolein, 16.5 g of 4-amidinobenzoic acid methyl ester hydrochloride and 7.5 g of sodium methylate were added to 150 ml of methanol, and the mixture was stirred overnight under N$_2$ stream at room temperature. The resultant precipitate was separated by filtration, and washed with water, methanol and ether. Then, 4.1 g of the thus obtained 4-(5-(4-butylphenyl)pyrimidine-2-yl)benzoic acid methyl ester was charged into a flask together with 41.5 g of 47% HBr aqueous solution. The mixture was stirred under heat and left standing for 35 hours at room temperature. Water was added thereto, and the resultant crystal was separated by filtration, recrystallized in ethanol-THF-benzene. The crystal was separated by filtration and dried.

1.0 g of the thus obtained 4-(5-(4-butylphenyl)-pyrimidine-2-yl)benzoic acid was charged in a flask together with 20 ml of thionyl chloride, and the mixture was refluxed under heat for 3 hours. After distilling of thionyl chloride, 20 ml of dry pyridine was added. While the resultant mixture being stirred under cooling with ice, a solution of (+)-2-dodecyloxypropanol 3.8 g in 20 ml of benzene was added dropwise to the mixture. After the addition, the mixture was stirred for 2 hours and left standing for 12 hours. After distilling off the solvent, the product was purified with a silica gel column chromatography with a benzene-THF solvent and further purified by recrystallization to obtain 0.7 g of 4-(5-(4'-butylphenyl)pyrimidine-2-yl)benzoic acid 2'-dodecyloxypropyl ester.

The following properties were observed.

DSC: Assuming a liquid crystal phase at 64°-136° C.

IR: 2910, 2850, 1720, 1440, 1280, 1100, 830, 760 cm$^{-1}$ $^1$H-NMR: 9 0, 8.6-8.1, 7.6-7.3, 4.4-4.3, 2.6-2.8, 1.6-1.4, 0.9-1.3.

EXAMPLE 31

(4-(5-heptylpyrimidine-2-yl)benzoic acid 2'-decyloxypropyl ester)

A mixture of 25 g of 2-heptylmalondialdehyde tetraethyl acetal, 40 ml of ethanol, 4 ml of water and 3 drops of conc. sunfuric acid was stirred for 20 hours at 50° C. and diluted with ether. After non-reacted 2-heptylmalondialdehyde tetraethyl acetal was removed by dil. Na$_2$CO$_3$ aqueous solution, ether was distilled off. 15 g of the thus obtained 2-heptyl-3-ethoxyacrolein, 17 g of 4-amidinobenzoic acid methyl ester hydrochloride and 8.0 g of sodium methylate were added to 150 ml of methanol, and the mixture was stirred overnight under N₂ stream at room temperature The resultant precipitate was separated by filtration, and washed with water, methanol and ether. Then, 3.9 g of the thus obtained 4-(5-(4-butyl-phenyl)pyrimidine-2-yl)benzoic acid methyl ester was charged into a flask together with 40.6 g of 47% HBr aqueous solution. The mixture was refluxed under heat and stirring for 5 hours and left standing for 17 hours at room temperature. Water was added thereto, and the resultant crystal was separated by filtration, recrystallized in ethanol. The crystal was separated by filtration and dried.

1.0 g of the thus obtained 4-(5-heptylpyrimidine-2-yl)benzoic acid was charged in a flask together with 20 ml of thionyl chloride, and the mixture was refluxed under heat for 2 hours. After distilling of thionyl chloride, 20 ml of dry pyridine was added. While the resultant mixture being stirred under cooling with ice, a solution of 1.9 g of (+)-2-decyloxypropanol in 20 ml of dry benzene was added dropwise to the mixture After the addition, the mixture was stirred for 3 hours and left standing for 15 hours. After distilling off the solvent, the product was purified with a silica gel column chromatography with a chloroform solvent and further purified by recrystallization in ethanol to obtain 0.4 g of 4-(5-heptylpyrimidine-2-yl)benzoic acid 2'-decyloxypropyl ester.

The following properties were observed.

DSC: Iso. $\xrightarrow{1.4° C.}$ Cryst.

IR: 2920, 2850, 1730, 1430, 1275, 1110, 760 cm⁻¹.
¹H-NMR: 8.1–8.6 ppm, 4.3 ppm, 3.5–3.8 ppm, 2.6–2.7 ppm, 0.9–1.6 ppm

EXAMPLE 32

(Property of liquid crystal composition containing mesomorphic compound prepared in Example 28)

A liquid crystal composition as shown in the following Table 4 was prepared and found to show a cholesteric phase in the range of 71°–61° C. and a smectic phase in the range of 61°–10° C. in the course of cooling.

TABLE 4

| Compound | wt. % |
|---|---|
| $C_8H_{17}O$—⌬—C(=O)—O—⌬—$OCH_2\overset{*}{C}H(CH_3)C_2H_5$ | 73.8 |
| $C_8H_{17}O$—⌬—O—C(=O)—⌬—⌬—$CH_2\overset{*}{C}H(CH_3)C_2H_5$ | 18.4 |
| $C_8H_{17}O$—⌬—⌬—$COOCH_2\overset{*}{C}H(CH_3)OC_7H_{15}$ | 7.8 |

EXAMPLE 33

(Property of liquid crystal composition containing mesomeorphic compound prepared in Example 30)

A liquid crystal composition as shown in the following Table 5 was prepared and found to show a liquid crystal phrase in the range of 5° C.–62° C. in the course of cooling.

TABLE 5

| Compound | wt. % |
|---|---|
| $C_8H_{17}O$—⌬—⌬—$COOCH_2\overset{*}{C}H(CH_3)C_2H_5$ | 89 |
| $C_4H_9$—⌬—(pyrimidine)—⌬—$COOCH_2\overset{*}{C}H(CH_3)OC_{12}H_{25}$ | 11 |

EXAMPLE 34

(Property of liquid crystal composition containing mesomorphic compound prepared in Example 31)

A liquid crystal composition as shown in the following Table 6 was prepared and found to show a cholesteric phase in the range of 61° to 54° C. and a smectic phase in the range of 54 to −14° C. in the course of cooling.

TABLE 6

| Compound | wt. % |
|---|---|
| $C_8H_{17}O$—⌬—C(=O)—O—⌬—$OCH_2\overset{*}{C}H(CH_3)C_2H_5$ | 71 |
| $C_8H_{17}O$—⌬—O—C(=O)—⌬—⌬—$CH_2\overset{*}{C}H(CH_3)C_2H_5$ | 18 |

TABLE 6-continued

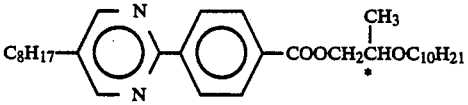

| | 11 wt. % |
|---|---|

A ferroelectric chiral smectic liquid crystal having an optically active group of the formula (A) or (B) has an excellent threshold characteristic in response to an electric field applied thereto, when used in a display device as proposed by N. A. Clark et al, so that it can provide a display device, which can be driven by a simple matrix electrode and can provide good contrast while preventing occurrence of crosstalk. This characteristic can also be attained by a liquid crystal composition containing a mesomorphic compound according to the present invention. Thus, the mesomorphic compound is particularly effective to provide a ferroelectric chiral smectic liquid crystal for use in a fine image and large screen display device.

When a device is constituted by using these materials, the device may be supported with a block of copper, etc., in which a heater is embedded in order to realize a temperature condition where the liquid crystal composition assumes a desired chiral smectic phase.

Figure 4:
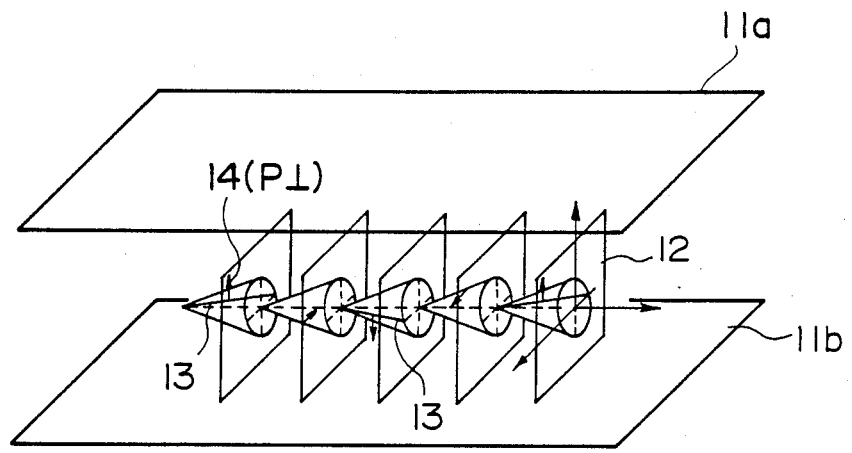
FIGS. 4 and 5 are schematic perspective views illustrating the basic operation principle of a liquid crystal device using a chiral smectic liquid crystal.

Referring to FIG. 4, there is schematically shown an example of a ferroelectric liquid crystal cell for explanation of the operation thereof. Reference numerals 11a and 11b denote base plates (glass plates) on which a transparent electrode of, e.g., In$_2$O$_3$, SnO$_2$, ITO (Indium-Tin Oxide), etc., is disposed respectively. A liquid crystal of a chiral smectic phase such as SmC* or SmH* in which liquid crystal molecular layers 12 are oriented perpendicular to surfaces of the glass plates is hermetically disposed therebetween. A full line 13 shows liquid crystal molecules. Each liquid crystal molecule 13 has a dipole moment (P⊥) 14 in a direction perpendicular to the axis thereof. When a voltage higher than a certain threshold level is applied between electrodes formed on the base plates 11a and 11b, a helical structure of the liquid crystal molecule 13 is loosened or unwound to change the alignment direction of respective liquid crystal molecules 13 so that the dipole moments (P⊥) 14 are all directed in the direction of the electric field. The liquid crystal molecules 13 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 5:
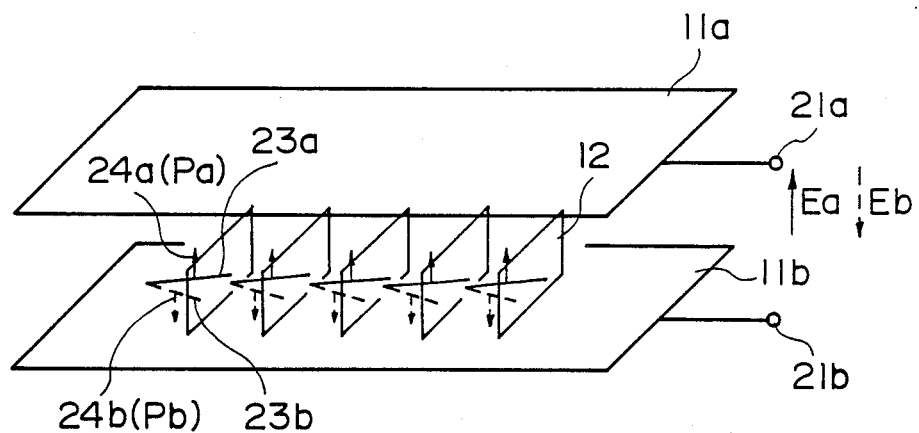

The liquid crystal layer in the liquid crystal device of the present invention may be rendered sufficiently thin in thickness (e.g., less than 10μ). As the thickness of the liquid crystal layer is decreased, the helical structure of the liquid crystal molecules is loosened even in the absence of an electric field whereby the dipole moment assumes either of the two states, i.e., Pa in an upper direction 24a or Pb in a lower direction 24b as shown in FIG. 5. When electric field Ea or Eb higher than a certain threshold level and different from each other in polarity as shown in FIG. 5 is applied to a cell having the above-mentioned characteristics, the dipole moment is directed either in the upper direction 24a or in the lower direction 24b depending on the ventor of the electric field Ea or Eb. In correspondence with this, the liquid crystal molecules are oriented to either a first stable state 23a or a second stable state 23b.

When the above-mentioned ferroelectric liquid crystal is used as an optical modulation element, it is possible to obtain two advantages as briefly touched on hereinbefore. First is that the response speed is quite fast. Second is that the orientation of the liquid crystal shows bistability. The second advantage will be further explained, e.g., with reference to FIG. 5. When the electric field Ea is applied to the liquid crystal molecules, they are oriented to the first stable state 23a. This state is kept stable even if the electric field is removed. On the other hand, when the electric field Eb of which direction is opposite to that of the electric field Ea is applied thereto, the liquid crystal molecules are oriented to the second stable state 23b, whereby the directions of molecules are changed. This state is similarly kept stable even if the electric field is removed. Further, as long as the magnitude of the electric field Ea or Eb being applied is not above a certain threshold value, the liquid crystal molecules are placed in the respective orientation states. In order to effectively realize high response speed and bistability, it is preferable that the thickness of the cell is as thin as possible.

The most serious problem encountered in forming a device using such a ferroelectric liquid crystal has been, as briefly mentioned hereinbefore, that it is difficult to form a cell having a highly uniform monodomain wherein liquid crystal layers having a chiral smectic phase such as SmC* or SmH* are aligned perpendicular to the base plate faces and the liquid crystal molecules are aligned almost in parallel with the base plate faces. A principal object of the invention is to provide a solution to this problem.

FIGS. 6A and 6B illustrate an example of the liquid crystal device according to the present invention. FIG. 6A is a plan view of the example and FIG. 6B is a sectional view taken along the line A—A in FIG. 6A.

A cell structure 100 shown in FIG. 6 comprises a pair of base plates 101a and 101b made of glass plates or plastic plates which are held with a predetermined gap with spacers 104 and sealed with an adhesive 106 to form a cell structure. On the base plate 101a is further formed an electrode group (e.g., an electrode group for applying scanning voltages of a matrix electrode structure) comprising a plurality of transparent electrodes 102a in a predetermined pattern, e.g., of a stripe pattern. On the base plate 101b is formed another electrode group (e.g., an electrode group for applying signal voltages of the matrix electrode structure) comprising a plurality of transparent electrodes 102b crossing the transparent electrodes 102a.

On the base plate 101b provided with such transparent electrodes 102b may be further formed an orientation controlling film 105 composed of an inorganic insulating material such as silicon monoxide, silicon dioxide, aluminum oxide, zirconia, magnesium fluoride, cerium oxide, cerium fluoride, silicon nitride, silicon carbide, and boron nitride, or an organic insulating material such as polyvinyl alcohol, polyimide, polyamide-imide, polyester-imide, polyparaxylylene, polyester, polycarbonate, polyvinyl acetal, polyvinyl chloride, polyamide, polystyrene, cellulose resin, melamine resin, urea resin and acrylic resin.

The orientation controlling film 105 may be formed by first forming a film of an inorganic insulating material or an organic insulating material as described above and then rubbing the surface thereof in one direction with velvet, cloth, paper, etc.

In another preferred embodiment according to the present invention, the orientation controlling film 105 may be formed as a film of an inorganic insulating material such as SiO or $SiO_2$ on the base plate 101a by the oblique or tilt vapor deposition.

Figure 8:
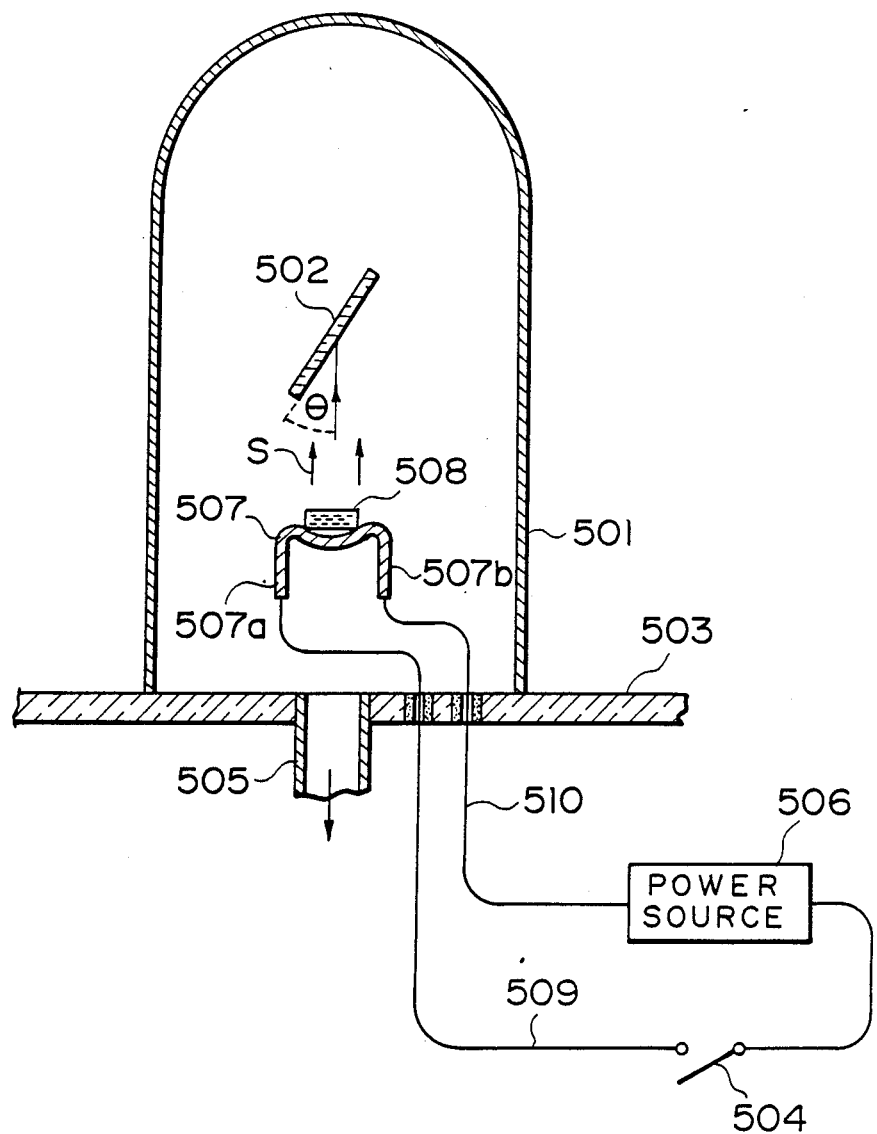
FIG. 8 is a sectional view schematically showing a tilt or oblique vapor deposition apparatus for use in production of the liquid crystal device according to the present invention.

In an apparatus shown in FIG. 8, a bell jar 501 is placed on an insulating base plate 503 provided with a suction hole 505 and the bell jar 501 is made vacuum by operating a vacuum pump (not shown) connected the suction hole 505. A crucible 507 made of tungsten or molybdenum is places inside and at the bottom of the bell jar 501. In the crucible 507 is placed several grams of a crystal 508 such as SiO, $SiO_2$ or $MgF_2$. The crucible 507 has two downwardly extending arms 507a and 507b, which are respectively connected to lead wires 509 and 510. A power source 506 and a switch 504 are connected in series to the lead wires 509 and 510 outside the bell jar 501. A base plate 502 is disposed inside the bell jar 501 and right above the crucible 507 so that it forms an angle of $\theta$ with respect to the vertical axis of the bell jar 501.

First, the bell jar 501 is evacuated to a vacuum of about $10^{-5}$ mmHg while the switch 504 is open. Then the switch 504 is closed to supply a power while adjusting an output of the power source 506 until the crucible is heated to an incandescent state of an appropriate temperature for evaporating the crystal 508. About 100 amps. of current is required for giving an appropriate temperature range (700°–1000° C.). The crystal 508 is then evaporated off to form an upward molecular stream denoted by S in the figure. The stream S is incident on the base plate 502 with an angle thereto of $\theta$ to coat the base plate 502. The angle $\theta$ is the above mentioned incident angle and the direction of the stream S is the "oblique or tilt vapor deposition direction". The thickness of the film is determined based on the calibration of the thickness with respect to the operation time which is effected prior to the introduction of the base plate 502 into the bell jar 501. After an appropriate thickness of the film is formed, a power supply from the source 506 is decreased, the switch 504 is opened, and the bell jar 501 and the interior thereof are cooled. Then, the pressure in the bell jar is raised to atmospheric pressure and the base plate 502 is taken out from the bell jar 501.

In still another embodiment, the orientation controlling film 105 may be formed by first forming a uniform film of the above-mentioned inorganic or organic insulating material on, i.e., in contact with or above, the base plate 101a and then subjecting the surface of the film to the oblique or tilt etching to provide the surface with an orientation controlling effect.

It is preferred that the orientation controlling film 105 is also caused to function as an insulating film. For this purpose, the orientation controlling film may preferably have a thickness in the range of 100 Å to 1 $\mu$, especially 500 Å to 5000 Å. The insulating film also has a function of preventing the occurrence of an electric current which is generally caused due to minor quantities of impurities contained in the liquid crystal layer 103, whereby deterioration of the liquid crystal material is prevented even on repeated operations.

In the liquid crystal device according to the present invention, it is possible to form an orientation controlling film similar to the orientation controlling film 105 also on the other base plate 101a.

In the cell structure shown in FIG. 6, the liquid crystal layer 103 may be formed into a chiral smectic phase such as SmC*, SmH*, SmI*, SmJ*, SmG* or SmF*. The liquid crystal layer 103 showing a chiral smectic phase may be formed by phase transition of a liquid crystal material on gradual cooling at a rate of, e.g., 1° C.-10° C./hour from a higher temperature phase such as cholesteric phase (chiral nematic phase), nematic phase or isotropic phase to SmA (smectic A phase) and then on further gradual cooling to the chiral smectic phase, or by phase transition on gradual cooling from such as higher temperature phase as cholesteric phase, etc., to the chiral smectic phase not through SmA.

As an important feature of the present invention, the liquid crystal material as described above may be formed into a monodomain of smectic phase. More specifically, the liquid crystal material, particularly a liquid crystal composition, may be composed so as to cause a successive phase transition of isotropic phase-cholesteric phase-SmA-chiral smectic phase, isotropic phase-cholesteric phase-chiral smectic phase or isotropic phase-SmA-chiral smectic phase.

FIG. 7 shows another embodiment of the liquid crystal device according to the present invention. In the liquid crystal device shown in FIG. 7, a plurality of spacer members 203 are disposed between a pair of base plates 101a and 101b. The spacer members 203 can be provided, for example, by forming a film of an inorganic compound such as SiO, $SiO_2$, $Al_2O_3$ and $TiO_2$, or a resin such as polyvinyl alcohol, polyimide, polyamideimide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin and a photoresist resin on the base plate 101a on which an orientation controlling film 105 has been provided, and by etching the film to leave the spacer members 203 at appropriate parts.

Such a cell structure 100 having base plates 101a and 101b as shown in FIG. 6 or FIG. 7 is sandwiched between a pair of polarizers 107 and 108 arranged in the form of cross nicols to form an optical modulation device causing optical modulation when a voltage is applied between electrodes 102a and 102b.

Next, an example of a memory-type line-by-line writing driving method using a ferroelectric liquid crystal is explained with reference to FIGS. 9-11.

Figure 9:
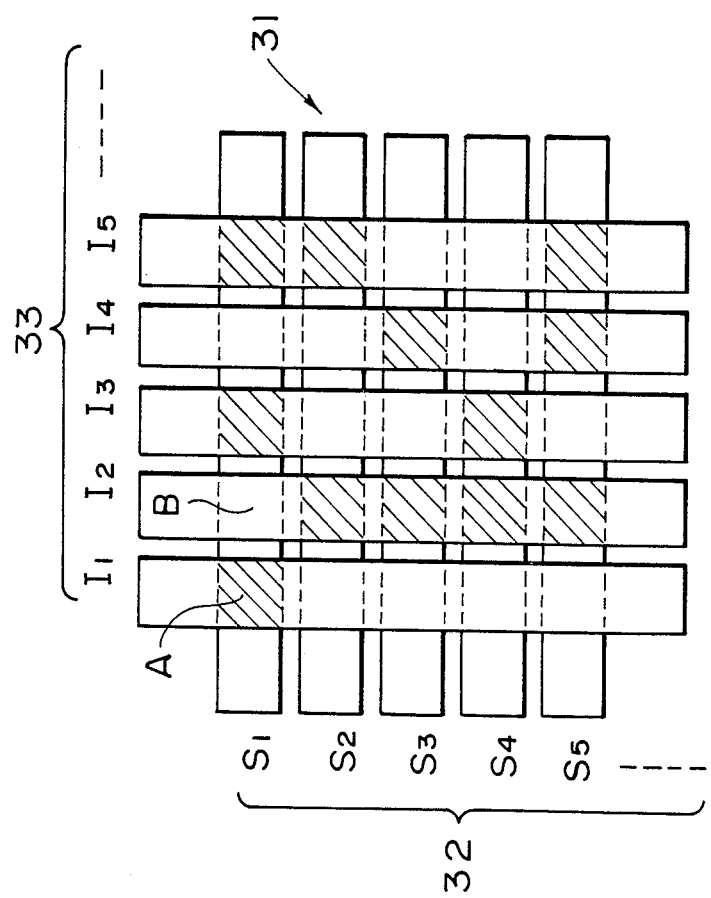
FIG. 9 is a schematic plan view showing an electrode arrangement of a liquid crystal device according to the present invention.
Figure 10A:
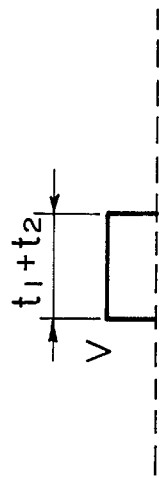
FIGS. 10A to 10D illustrate signals for driving a liquid crystal device according to the present invention.
Figure 10B:
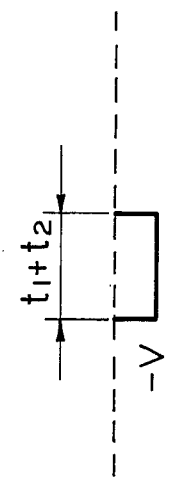

Referring to FIG. 9, there is schematically shown an example of a cell 31 having a matrix electrode arrangement in which a ferroelectric liquid crystal material (not shown) is interposed between a pair of groups of electrodes oppositely spaced from each other. Reference numerals 32 and 33 respectively denote a group of scanning electrodes to which scanning signals are applied and a group of signal electrodes to which information signals are applied. Referring to FIGS. 10A and 10B, there are respectively shown electric signals applied to a selected scanning electrode $S_1$ and electric signals applied to the other scanning electrodes (non-selected scanning electrodes) $S_2$, $S_3$, $S_4$.

Figure 10C:
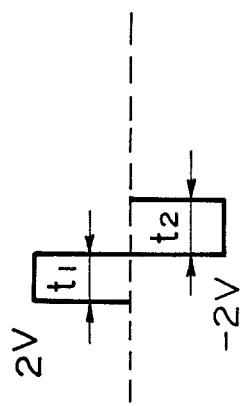
Figure 10D:
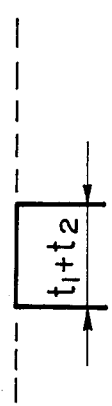

On the other hand, FIGS. 10C and 10D show electric signals applied to the selected signal electrode $I_1$, $I_3$, $I_5$ and electric signals applied to the nonselected signal electrodes $I_2$, $I_4$, respectively. In FIGS. 10A to 10D and 11A to 11D, the abscissa and the ordinate represent a time and a voltage, respectively. For instance, when displaying a motion picture, the group of scanning electrodes 32 are sequentially and periodically selected. If a threshold voltage for giving a first stable state of the liquid crystal having bistability is referred to as $-V_{th1}$ and a threshold voltage for giving a second stable state thereof as $+V_{th2}$, an electric signal applied to the selected scanning electrode 42($S_1$) is an alternating voltage showing 2V at a phase (time) $t_1$ and $-2V$ at a phase (time) $t_2$, as shown in FIG. 10A. When such an electric signal having plural phases of mutually different voltages is applied to a selected scanning electrode, an important effect can be obtained that conversion between the first and second stable states corresponding to optically "bright" and "dark" states, respectively, can be quickly caused.

On the other hand, the other scanning electrodes $S_2$-$S_5$... are grounded as shown in FIG. 10B. Accordingly, the electric signals appearing thereon show zero volt. On the other hand, an electric signal applied to the selected signal electrode $I_1$, $I_3$, $I_5$ shows V as indicated in FIG. 10C while an electric signal applied to the non-selected signal electrode $I_2$, $I_4$ shows $-V$ as indicated in FIG. 10D. In this instance, the voltage V is set to a desired value which satisfies $V < V_{th\ 2} < 3V$ and $-3V < -V_{th\ 1} < -V$. Voltage waveforms applied to picture elements A and B, for example, among the picture elements shown in FIG. 9 when such electric signals are given are shown in FIGS. 11A and 11B, respectively. Namely, as seen from FIG. 11A, a voltage of 3V above the threshold level $V_{th\ 2}$ is applied to the ferroelectric liquid crystal at the picture elements A on the selected scanning line at a phase $t_2$. Further, a voltage of $-3V$ exceeding the threshold level $-V_{th1}$ is applied to the ferroelectric liquid crystal at the picture elements B on the same scanning line at a phase $t_1$. Accordingly, depending upon whether a signal electrode is selected or not on a selected scanning electrode line, the orientation of liquid crystal molecules changes. Thus, when a certain signal electrode is selected, the liquid crystal molecules are oriented to the first stable state, while when not selected, oriented to the second stable state. In either case, the orientation of the liquid crystal molecules is not related to the previous states of each picture element.

On the other hand, as shown in FIGS. 11C and 11D, the voltage applied to all the picture elements on the non-selected scanning lines is $+V$ or $-V$, each not exceeding the threshold level. Accordingly, the ferroelectric liquid crystal molecules electrically connected to the respective picture elements on the non-selected scanning lines are placed in the orientations corresponding to signal states produced when they have been last scanned without change in orientation. Namely, when a certain scanning electrode is selected, signals corresponding to one line are written and thus writing of signals corresponding to one frame is completed. The signal state of each picture element can be maintained until the line is subsequently selected. Accordingly, even if the number of scanning lines increases, the duty ratio does not substantially change, resulting in no possibility of lowering in contrast, occurrence of crosstalk, etc.

Then, a possible problem which can occur when a device as described above is actually driven as a display device, is considered. Referring to FIG. 9, it is assumed that, among the picture elements formed at intersections of the scanning electrodes $S_1$-$S_5$... and the signal electrodes $I_1$-$I_5$, the picture elements with hatching are in the "bright" state and picture elements drawn in white are in the "dark" state. When display states on a signal electrode $I_1$ in FIG. 9 are noted, a picture element (A) on a scanning electrode $S_1$ is in the "bright" state, and the other picture elements (B) are all in the "dark" state. As a driving mode for obtaining such a display plate, FIG. 12 shows an example of the scanning signals, an information signal applied to a signal electrode $I_1$ and a voltage applied to the picture element A in time series.

Figure 12:
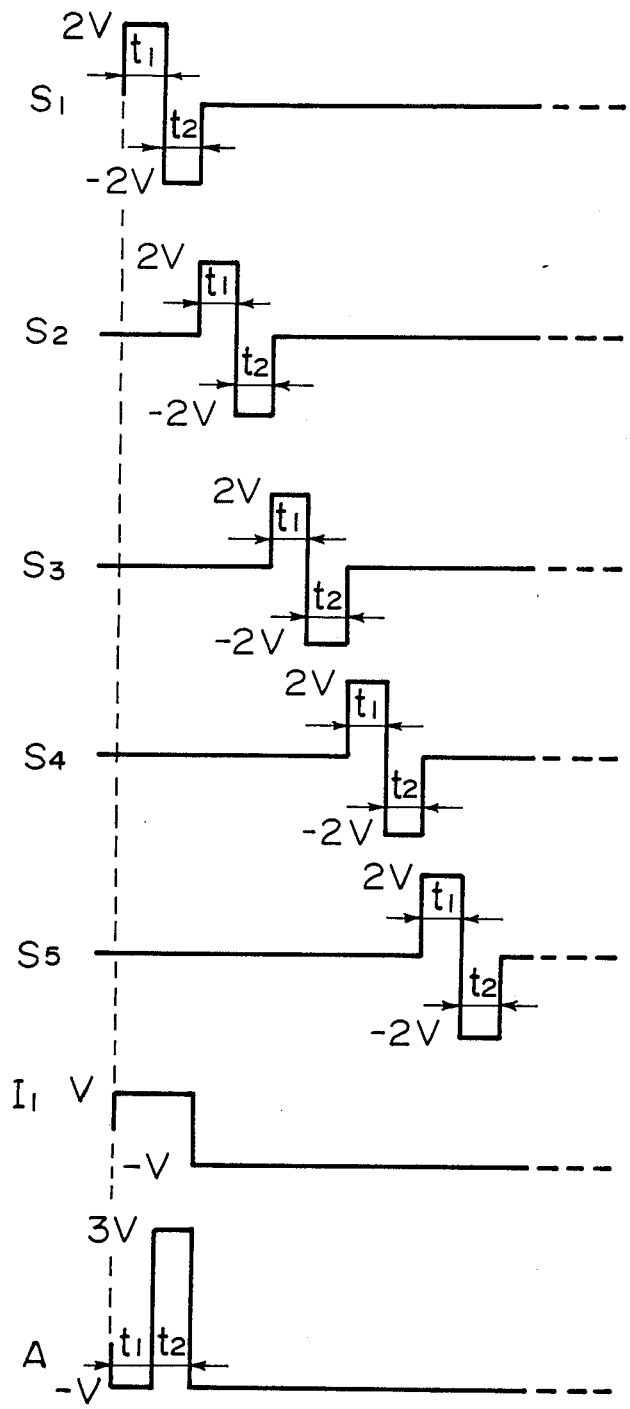
FIG. 12 illustrates waveforms applied in time series to a liquid crystal device according to the present invention.

In the driving mode shown in FIG. 12, when a scanning electrode $S_1$ is scanned, a voltage of 3V exceeding the threshold voltage $V_{th2}$ is applied to the picture element A at time $t_2$, so that the picture element A is oriented or switched to one stable state, i.e., the bright state, regardless of its previous state. After that, during the period when a scanning electrodes $S_2$-$S_5$... are scanned, a voltage of $-V$ is continually applied and the picture element A is expected to keep its "bright" state as the voltage $-V$ does not exceed the threshold voltage $-V_{th1}$. As a matter of actual problem, however, when one direction of signal (one for providing "dark" state in this case) is continually applied to one signal electrode, a reversal of display states can occur especially in a case where a very large number of scanning lines are used and a high speed driving is pursued. Such a reversal phenomenon can be effectively prevented by using the above mentioned specific mesomorphic or liquid crystal compound or a liquid crystal composition containing the same.

Some examples of preparation of the liquid crystal device will now be explained.

EXAMPLE 35

On a square glass base plate were formed ITO (Indium-Tin-Oxide) electrode films in the form of stripes with a width of 62.5 μm at a pitch of 100 μm. In an apparatus for the oblique vapor deposition as shown in FIG. 8, the base plate was disposed with its face having the ITO film being directed downward and a crystal of $SiO_2$ was set in a crucible of molybdenum. Then the vapor deposition apparatus was evacuated to a vacuum of the order of $10^{-5}$ mmHg and $SiO_2$ was obliquely vapor-deposited in a prescribed manner to form an electrode plate with an 800 μ-thick oblique vapor deposition film (A electrode plate).

On the other hand, on a similar glass plate provided with stripe-form ITO electrode films was applied a polyimide-forming solution ("PIQ" produced by Hitachi Kasei Kogyo K.K.; Non-volatile content: 14.5 wt. %) by means of a spinner coater, which was then heated at 120° C. for 30 minutes to form a film of 800 Å in thickness (B electrode plate).

Then, a heat-setting epoxy adhesive was applied to the periphery of the A electrode plate except for the portion forming an injection port by screen printing process. The A electrode plate and the B electrode plate were superposed with each other so that their stripe-pattern electrodes crossed each other with right angles and secured to each other with a polyimide spacer while leaving the gap of 2 μ therebetween, thereby to form a cell (blank cell).

A liquid crystal composition A as shown below was heated into isotropic phase and injected through the injection port of the above-prepared cell, and the injection port was sealed. The liquid crystal cell thus formed was gradually cooled at a rate of 0.5° C./hr and was observed through a microscope while being sandwiched between a pair of polarizers arranged in a cross nicol relationship, whereby a monodomain of SmC* phase with non-spiral structure and free of orientation defects was found to be formed.

| Composition A | |
|---|---|
| C8H17O—⌬—C(=O)—O—⌬—OCH2CHC2H5 (CH3) * | 60 wt. % |
| C8H17O—⌬—O—C(=O)—⌬—⌬—CH2CHC2H5 (CH3) * | 30 wt. % |
| C8H17O—⌬—N=N(O)—⌬—OCCHOC7H15 (CH3, =O) * | 10 wt. % |

EXAMPLE 36

On two square glass plates each provided with stripe-form ITO electrode films as used in Example 1 was respectively applied a polyimide-forming solution (the same as the one used in Example 1) by means of a spinner coater, which was then heated at 120° C. for 30 minutes, at 200° C. for 60 minutes and at 350° C. for 30 minutes to form a film of 800 Å in thickness. The polyimide films on the thus obtained two electrode plates were respectively subjected to rubbing treatment with velvet in one direction so that, when the two electrodes plates were superposed each other, their rubbing directions are parallel with each other and their stripe form ITO electrodes cross each other at right angles.

Then, a heat-setting epoxy adhesive was applied to the periphery of one electrode plate except for the portion forming an injection port by screen printing process, the other electrode plate was superposed thereon in the arrangement described above, and the two electrode plates were secured to each other with a polyimide spacer while leaving the gap of 2 μ therebetween.

Into the thus prepared cell was injected the above described liquid composition A and the injection port was sealed. The liquid crystal cell thus formed was gradually cooled and was observed through a microscope while being sandwiched between a pair of polarizers arranged in a cross nicol relationship, whereby a monodomain of SmC* phase with non-spiral structure and free of orientation defects was found to be formed.

EXAMPLES 37 AND 38

Ferroelectric liquid crystal devices were prepared in the same manner as in Example 36 except that the liquid crystal composition A was replaced by the following liquid crystal composition B (Example 37) and liquid crystal composition C (Example 38), respectively.

When these ferroelectric liquid crystal devices were observed through a polarization microscope, a monodomain of non-spiral structure free of orientation defects was respectively confirmed to be formed.

| Compostion B | |
|---|---|
| DOBAMBC | 88 wt. % |
| 4'-octyl-4-α-heptyloxypropanoyloxyazobenzene | 12 wt. % |

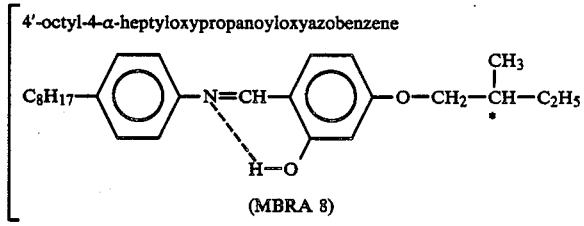

| Compostion C | |
|---|---|
| 4'-octyl-4-α-heptyloxypropanoyloxyazobenzene | 2 wt. % |
| C8H17—⌬—N=CH—⌬(H—O)—O—CH2—CH(CH3)—C2H5 * (MBRA 8) | 98 wt. % |

EXAMPLE 39

Into a cell prepared in the same manner as in Example 35 was injected the following liquid crystal composition in isotropic phase. After sealing, the thus prepared cell was gradually cooled, whereby a monodomain of SmC* free of orientation defects was found to be formed.

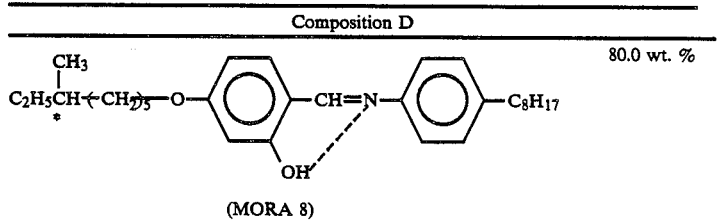

Composition D

C2H5CH(CH3)(CH2)3—O—⌬—CH=N—⌬—C8H17 (OH) * (MORA 8) — 80.0 wt. %

-continued

| Composition D | |
|---|---|
| 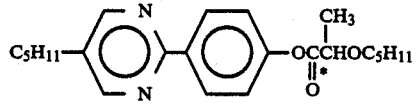 | 20.0 wt. % |

EXAMPLE 40

Into a cell prepared in the same manner as in Example 35 was injected the following liquid crystal composition E in isotropic phase. After sealing, the thus prepared cell was gradually cooled, whereby a monodomain of SmC* free of orientation defects was found to be formed.

| Composition E | |
|---|---|
| 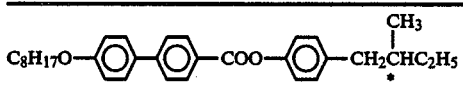 (80SI*) | 85 wt. % |
| 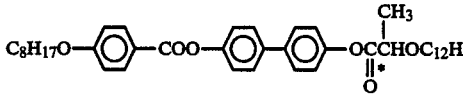 | 15 wt. % |

EXAMPLE 41

Into a cell prepared in the same manner as in Example 35 was injected the following liquid crystal composition F in isotropic phase. After sealing, the thus prepared cell was gradually cooled, whereby a monodomain of SmC* free of orientation defects was found to be formed.

| Composition F | |
|---|---|
| MORA 8 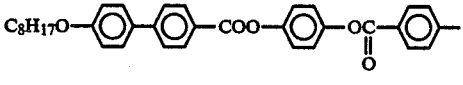  | 80 wt. % 20 wt. % |

EXAMPLE 42

Into a cell prepared in the same manner as in Example 35 was injected the following liquid crystal composition G in isotropic phase. After sealing, the thus prepared cell was gradually cooled, whereby a monodomain of SmC* free of orientation defects was found to be formed.

| Composition G | |
|---|---|
| 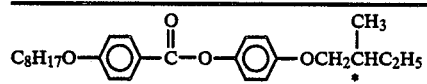 | 73.8 wt. % |
| 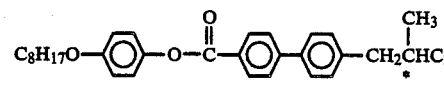 | 18.4 wt. % |
| 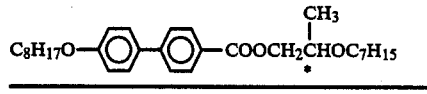 | 7.8 wt. % |

EXAMPLE 43

Into a cell prepared in the same manner as in Example 36 was injected the liquid crystal composition G used in Example 42 in isotropic phase. After sealing, the thus prepared cell was gradually cooled, whereby a monodomain of SmC* free of orientation defects was found to be formed.

EXAMPLES 44 AND 45

Ferroelectric liquid crystal devices were prepared in the same manner as in Example 36 except that the liquid crystal composition A was replaced by the following liquid crystal composition H (Example 44) and liquid crystal composition I (Example 45).

When these ferroelectric liquid crystal devices were observed through a polarization microscope, a monodomain of non-spiral structure free of orientation defects was respectively confirmed to be formed.

Composition H

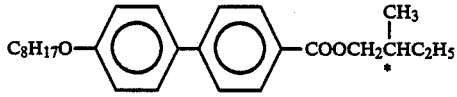  89 wt. %

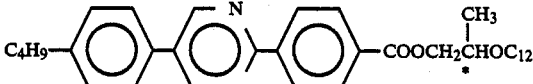  11 wt. %

Composition I

-continued

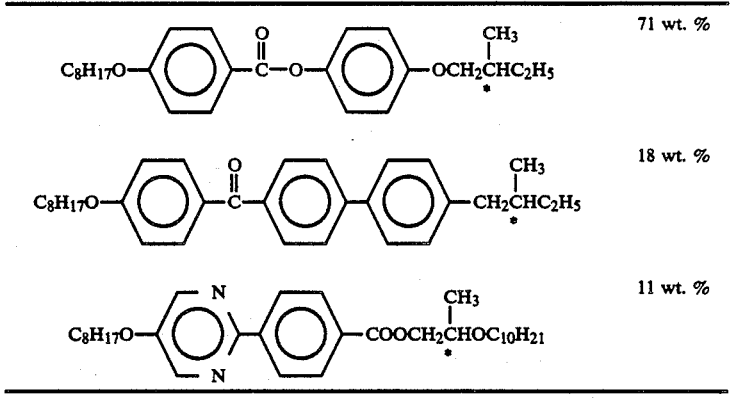

| | |
|---|---|
| | 71 wt. % |
| | 18 wt. % |
| | 11 wt. % |

EXAMPLE 46

On two electrode plates with stripe-form electrodes designed to cross each other to form opposite matrix electrodes, a 5 wt. % solution of a polyamic acid resin (reaction product of pyromellitic anhydride and 4,4'-diaminodiphenyl ether) in N-methylpyrrolidone was applied and heated to 250° C. to cause ring-closure reaction to form a 100 Å-thick polyimide film. The polyimide films on the two electrode were respectively rubbed in one direction, and the electrode plates were fixed to each other so that their rubbed directions were in parallel with each other to form a cell.

Then, a liquid crystal composition J shown below in isotropic phase was injected into the above cell by vacuum injection method. After sealing, the cell was gradually cooled at a rate of 0.5° C./hr to prepare a liquid crystal cell of SmC*.

A polarizer and an analyzer were disposed on both sides of the liquid crystal cell in a cross nicol relationship, and signals having waveforms as shown in FIGS. 10 and 11 were applied to the matrix electrodes. The scanning signal was an alternating waveform of +8 volts and −8 volts as shown in FIG. 10A, the writing signals were +4 volts and −4 volts, respectively, the writing pulse duration was 500 μsec., and the one-frame period was 30 msec.

As a result of the memory-drive type line-by-line writing operation as described hereinbefore under these conditions, this liquid crystal device provided a normal motion picture display without causing reversal of written states.

EXAMPLES 47–49

Liquid crystal devices were prepared in the same manner as in Example 46 except that the liquid crystal composition J was replaced by liquid crystal compositions K (Example 47), L (Example 48) and M (Example 49), respectively, shown below. The liquid crystal devices were respectively used for motion picture display as explained in Example 46, whereby no reversal phenomenon was observed in any of the pictures.

Composition J

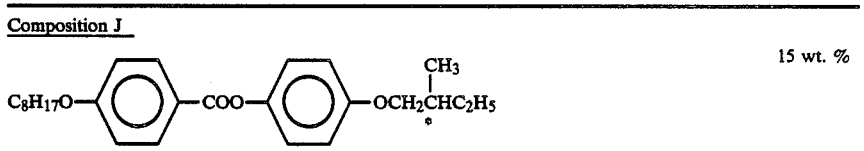

| | |
|---|---|
| | 15 wt. % |
| | 70 wt. % |
| | 15 wt. % |

Composition K

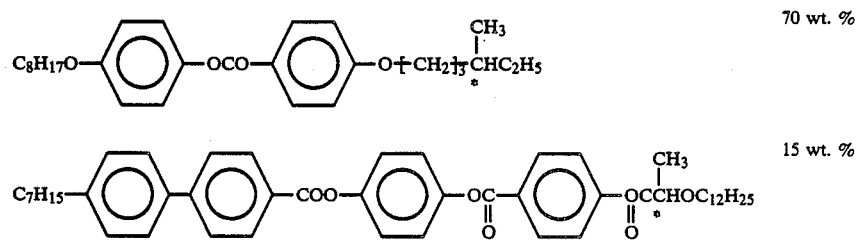

MORA8   70 wt. %

30 wt. %

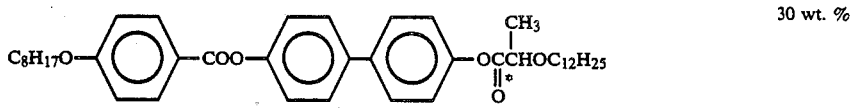

Composition L

-continued

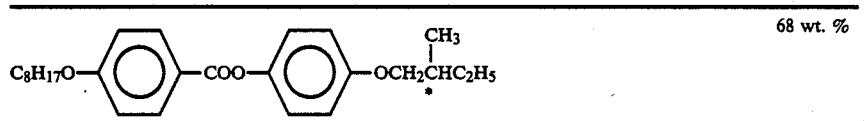 68 wt. %

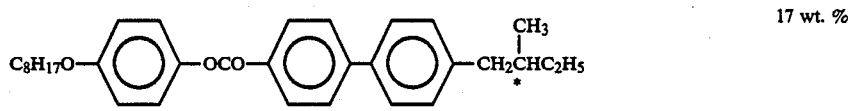 17 wt. %

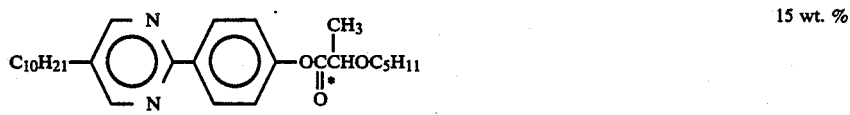 15 wt. %

Composition M
MBRA8    80 wt. %

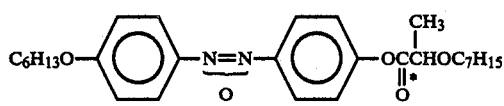

COMPARATIVE EXAMPLES 1 AND 2

Comparative liquid crystal compositions J' (Comparative Example 1) and L'(Comparative Example 2) were prepared by omitting the compounds having an optically active group represented by the formula (A) from the liquid crystal compositions J and L used in Examples 46 and 48, respectively. Liquid crystal devices were respectively prepared by using these comparative examples and driven in the same manner as described above, whereas normal motion pictures could not be formed because reversal phenomena occurred.

EXAMPLES 50-53

Liquid crystal devices were prepared in the same manner as in Example 46 except that the liquid crystal composition J was replaced by the liquid crystal compositions N (Example 50), 0 (Example 51), P (Example 52) and Q (Example 53), respectively, shown below. The liquid crystal devices were respectively used for motion picture display as explained in Example 46, whereby no reversal phenomenon was observed in any of the pictures.

Comparative Composition J'

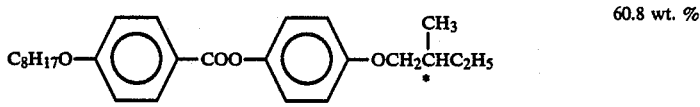 60.8 wt. %

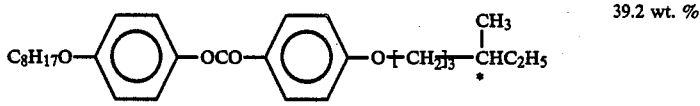 39.2 wt. %

Comparative Composition L'

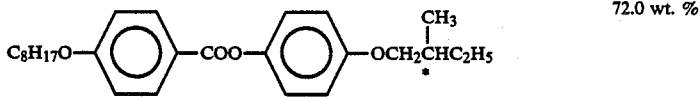 72.0 wt. %

 28.0 wt. %

Composition N
MORA 8    80 wt. %

-continued

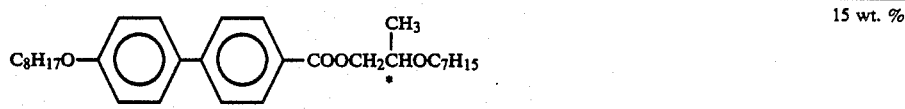 15 wt. %

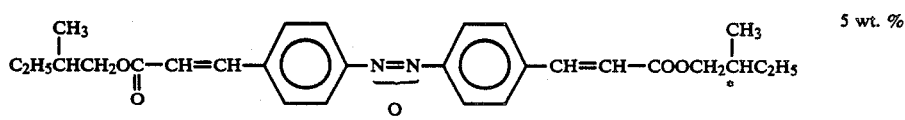 5 wt. %

Composition O
MBRA8 70 wt. %

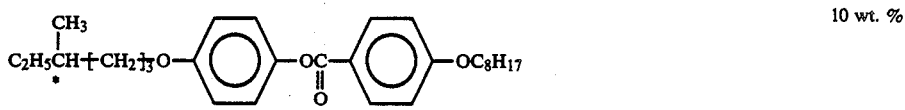 10 wt. %

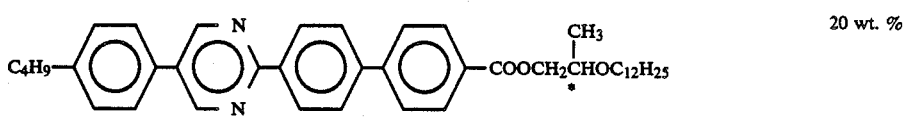 20 wt. %

Composition P

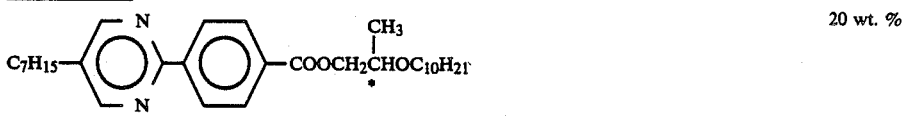 20 wt. %

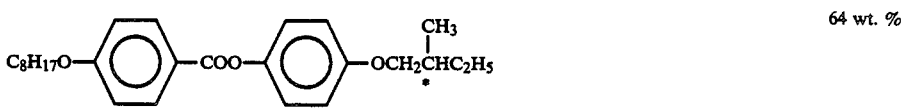 64 wt. %

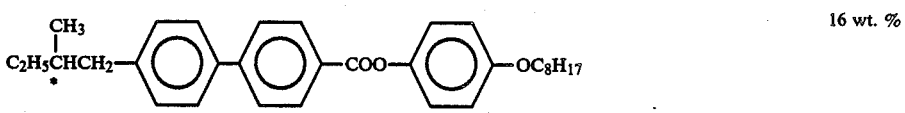 16 wt. %

Composition Q

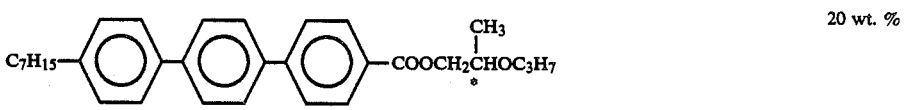 20 wt. %

MORA8 60 wt. %

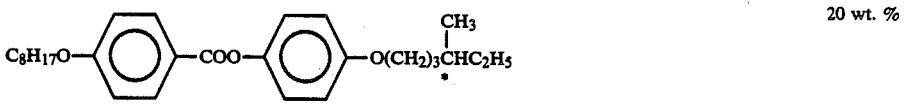 20 wt. %

COMPARATIVE EXAMPLES 3 AND 4

Comparative liquid crystal compositions P′ (Comparative Example 3) and Q′ (Comparative Example 4) were prepared by omitting the compounds having an optically active group represented by the formula (B) from the liquid crystal compositions P and Q used in Examples 52 and 53, respectively. Liquid crystal devices were respectively prepared by using these comparative examples and driven in the same manner as described above, whereas normal motion pictures could not be formed because reversal phenomena occurred.

Comparative Example P′

-continued

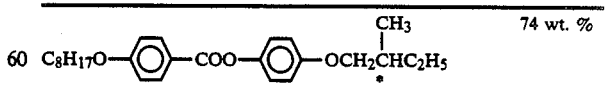 74 wt. %

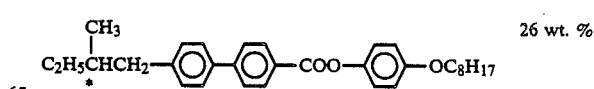 26 wt. %

Comparative Composition Q′
MORA 8 70 wt. %

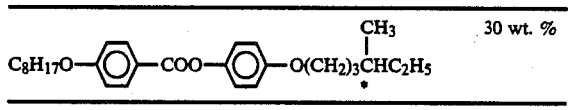

As described hereinabove, the lactic acid derivative according to the present invention can be combined with an intermediate of a functional material having an appropriate intermolecular force and shape without imparing an optical activity and allows arbitrary molecular design. Further, a particular class of the lactic acid derivative according to the present invention can vary the length of the alkyl group therein and, because of this feature, is capable of controlling the kind of and the temperature range for a liquid crystal phase in its mesomorphic state, whereby an excellent liquid crystal composition can be provided. The lactic acid derivative according to the present invention is also capable of readily controlling the hydrophobic group and is effective for producing an accumulated film of single molecular layers according to the LB film process.

Further, the present invention provides a smectic phase free of orientation defects by using the above mentioned specific class of mesomorphic compound, particularly a ferroelectric liquid crystal phase of non-spiral structure free of orientation defects.

Further, the ferroelectric liquid crystal device according to the present invention has an advantageous feature that a reversal phenomenon which has occurred when switching or display is performed by a timesharing driving method of the memory driving type can be effectively prevented by using a mesomorphic compound having an optically active group as described above or a liquid crystal composition containing the same.

What is claimed is:

1. An optically active lactic acid derivative represented by the formula

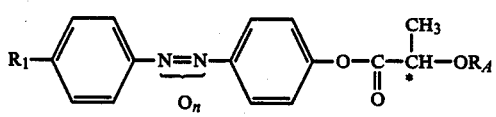

wherein $R_1$ is an alkyl or alkoxy group having 1 to 20 carbon atoms, $R_A$ is an alkyl group having 1 to 20 carbon atoms, n is 0 or 1, and C with * is an asymmetric carbon atom.

2. A lactic acid derivative according to claim 1, which is a compound represented by the following formula (1):

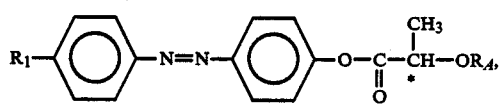

wherein $R_A$ is a linear alkyl group.

3. A lactic acid derivative according to claim 1, which is a compound represented by the following formula (2):

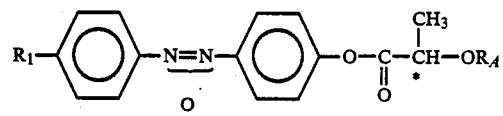

wherein $R_A$ is a linear-alkyl group.

4. A lact,ic acid derivative according to claim 2, which is 4'-hexyl-4-α-butoxypropanoyloxyazobenzene.

5. A lactic acid derivative according to claim 2, which is 4'-heptyl-4-α-bytoxypropanoyloxyazobenzene.

6. A lactic acid derivative according to claim 2, which is 4'-octyl-4-α-butoxypropanoyloxyazobenzene.

7. A lactic acid derivative according to claim 2, which is 4'-hexyl-4-α-bytoxypropanoyloxyazobenzene.

8. A lactic acid derivative according to claim 2, which is 4'-octyl-4-α-heptyloxypropanoyloxyazobenzene.

9. A lactic acid derivative according to claim 2, which is 4'-hexyloxy-4-α-heptyloxypropanoyloxyazobenzene.

10. A lactic acid derivative according to claim 3, which is 4'-hexyloxy-4-α-butoxypropanoyloxyazoxybenzene.

11. A lactic acid derivative according to claim 3, which is 4'-octyl-4-α-heptyloxypropanoyloxyazoxybezene.

12. A lactic acid derivative according to claim 3, which is 4'-hexyloxy-4-α-heptyloxypropanoyloxyazoxybenzene.

13. A liquid crystal composition comprising 0.01 to 100 parts by weight of a lactic acid derivative according to claim 1, and 100 parts by weight of another liquid crystal component selected from the group consisting of ferroelectric liquid crystals and cholesteric liquid crystals.

14. A liquid crystal composition according to claim 13, wherein said another liquid crystal component is a Schiff base-type ferroelectric liquid crystal compound.

15. A liquid crystal composition according to claim 13, wherein said another liquid crystal component is an ester-type ferroelectric liquid crystal compound.

16. A liquid crystal composition according to claim 13, wherein said another liquid crystal component is an azoxy-type ferroelectric liquid crystal compound.

17. A liquid crystal composition according to claim 13, wherein said another liquid crystal component is a biphenyl-type ferroelectric liquid crystal compound.

18. A liquid crystal composition according to claim 13, wherein said another liquid crystal component is a liquid crystal material showing cholesteric phase.

19. A liquid crystal composition according to claim 13 wherein said another liquid crystal component is a liquid crystal material showing a chiral smectic phase.

20. A liquid crystal composition according to claim 19, wherein said chiral smectic phase is chiral smectic C phase.

21. A liquid crystal device comprising a pair of base plates and a liquid crystal material having a smectic phase and a higher temperature phase; said liquid crystal material comprising a mesomorphic, optically active lactic acid derivative represented by the formula

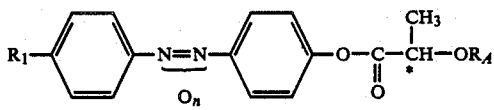

wherein $R_1$ is an alkyl or alkoxy group having 1 to 20 carbon atoms, $R_A$ is an alkyl group having 1 to 20 carbon atoms, n is 0 or 1, and C with * is an asymmetric carbon atom.

22. A liquid crystal device according to claim 21, wherein said mesomorphic compound is a compound represented by the following formula (1):

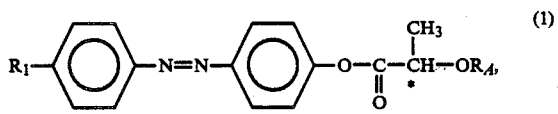

wherein $R_A$ is a linear alkyl group.

23. A liquid crystal device according to claim 21, wherein said mesomorphic compound is a compound represented by the following formula (2):

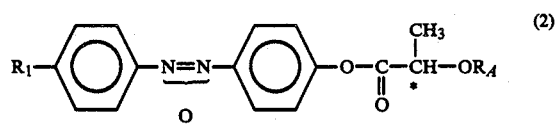

wherein $R_A$ is a linear alkyl group.

24. A liquid crystal device according to claim 21, wherein at least one of said pair of base plates has a surface having an effect of orienting the direction of the molecular axes of liquid crystal molecules constituting the liquid crystal material contacting the surface preferentially in one direction.

25. A liquid crystal device according to claim 24, where said orientation effect has been imparted by rubbing.

26. A liquid crystal device according to claim 24, wherein said orientation effect has been provided with a film formed by oblique vapor deposition.

27. A liquid crystal device according to claim 21, wherein said higher temperature phase is isotropic phase, cholesteric phase or nematic phase.

28. A liquid crystal device according to claim 21, wherein said liquid crystal material causes successive phase transition of isotrophic phase, cholesteric phase, smectic A phase and a chiral smectic phase in the order named upon temperature decreases.

29. A liquid crystal device according to claim 21, wherein said liquid crystal material causes successive phase transition of isotropic phase, cholesteric phase and chiral smectic phase in the order named upon temperature decrease.

30. A liquid crystal device according to claim 21 wherein said liquid crystal material causes successive phase transition of isotropic phase, smectic A phase and a chiral smectic phase in the order named upon temperature decrease.

31. A liquid crystal device according to claim 21 which comprises a plurality of picture elements arranged in a plurality of rows, each picture element comprising a pair of oppositely spaced electrodes, said liquid crystal material being disposed between the pair of electrodes, wherein said device is adapted for a line-by-line driving scheme wherein a writing signal is applied to said plurality of picture elements row by row in a writing cycle, and the thus written states of a particular row of picture elements are retained until a fresh writing signal is applied to the particular row of picture elements in a subsequent writing cycle.

* * * * *

UNITED STATES PATENT AND TRADEMARK OFFICE
CERTIFICATE OF CORRECTION

PATENT NO. : 4,775,223

DATED : October 4, 1988

INVENTOR(S) : KAZUO YOSHINAGA, ET AL.          Page 1 of 5

It is certified that error appears in the above-identified patent and that said Letters Patent is hereby corrected as shown below:

COLUMN 6

Lines 37-39, 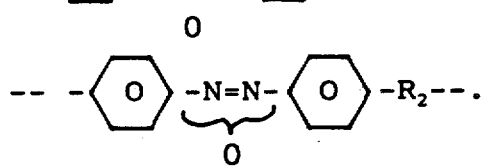 should read

COLUMN 7

Line 12, "acyclic" should read --cyclic--.

Line 27, "branched alkynyls, branched alkynyls" should read --branched alkynyls, cycloalkynyls--.

COLUMN 8

Line 66, "$C_9H_{19}$" should read --$C_9H_{19}$- --.

UNITED STATES PATENT AND TRADEMARK OFFICE
CERTIFICATE OF CORRECTION

PATENT NO. : 4,775,223
DATED : October 4, 1988
INVENTOR(S) : KAZUO YOSHINAGA, ET AL.

It is certified that error appears in the above-identified patent and that said Letters Patent is hereby corrected as shown below:

COLUMN 14

Line 57, "(S-4-O-" should read --(S-4-o- --.

Line 57, "butylresorcilidene" should read --butylresorcylidene--.

COLUMN 15

Line 11, "(S-4-O-" should read --(S-4-o- --.

COLUMN 18

Line 53, "=-IR:" should read --=-32°, IR:--.

Line 58, "L-+(.)-" should read --L-(+)- --.

COLUMN 19

Line 46, "-4-a-" should read --4-α- --.

COLUMN 20

Lines 2-3, "heptylazaobenzene" should read --heptylazobenzene--.

UNITED STATES PATENT AND TRADEMARK OFFICE
CERTIFICATE OF CORRECTION

PATENT NO. : 4,775,223
DATED : October 4, 1988
INVENTOR(S) : KAZUO YOSHINAGA, ET AL.

It is certified that error appears in the above-identified patent and that said Letters Patent is hereby corrected as shown below:

COLUMN 22

Lines 54-56, 

should read

COLUMN 29

Lines 47-48, "heptyloxybenzenepropyloctyloxybiphenyl-" should read --heptyloxypropyloctyloxybiphenyl- --.

COLUMN 30

Line 57, "9 0," should read --9.0,--.

COLUMN 41

Lines 46-49, "CH$_3$
             |
          -CCHOC$_8$H$_17$"    should read    -OCCHOC$_8$H$_17$ --.
             ||*                                ||*
             O                                  O (with CH$_3$ above)

UNITED STATES PATENT AND TRADEMARK OFFICE
CERTIFICATE OF CORRECTION

PATENT NO. : 4,775,223
DATED : October 4, 1988
INVENTOR(S) : KAZUO YOSHINAGA, ET AL.

It is certified that error appears in the above-identified patent and that said Letters Patent is hereby corrected as shown below:

COLUMN 43

Lines 8-10, "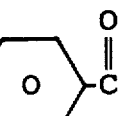" should read

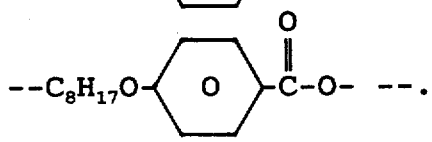 --.

COLUMN 46

Lines 19-24, "80 wt.%" should read --80 wt. %--.

20 wt. %

COLUMN 50

Line 9, "lact, ic" should read --lactic--.

Line 12, "bytoxypropanoyloxyazoben-" should read --butoxypropanoyloxyazoben- --.

Line 17, "bytoxypropanoyloxyazobenzene" should read --heptyloxypropanoyloxyazobenzene--.

Line 58, "13" should read --13,--.

UNITED STATES PATENT AND TRADEMARK OFFICE
CERTIFICATE OF CORRECTION

PATENT NO. : 4,775,223

DATED : October 4, 1988

INVENTOR(S) : KAZUO YOSHINAGA, ET AL.   Page 5 of 5

It is certified that error appears in the above-identified patent and that said Letters Patent is hereby corrected as shown below:

COLUMN 52

Line 4, "where" should read --wherein--.

Line 16, "decreases" should read --decrease--.

Line 22, "claim 21" should read --claim 21,--.

Line 27, "claim 21" should read --claim 21,--.

Signed and Sealed this

Twenty-eighth Day of November 1989

*Attest:*

JEFFREY M. SAMUELS

*Attesting Officer*   Acting Commissioner of Patents and Trademarks